United States Patent
Makhseed et al.

(10) Patent No.: US 10,723,694 B2
(45) Date of Patent: Jul. 28, 2020

(54) PROPARGYL-FUNCTIONALIZED MACROCYCLIC COMPOUNDS

(71) Applicant: KUWAIT UNIVERSITY, Safat (KW)

(72) Inventors: Saad A. Makhseed, Safat (KW); Ali A. Husain, Safat (KW); Asaithampi Ganesan, Safat (KW); Mahmut Durmus, Gebze-Kocaeli (TR)

(73) Assignee: Kuwait University, Safat (KW)

( * ) Notice: Subject to any disclaimer, the term of this patent is extended or adjusted under 35 U.S.C. 154(b) by 0 days.

(21) Appl. No.: 16/149,317

(22) Filed: Oct. 2, 2018

(65) Prior Publication Data

US 2020/0102267 A1   Apr. 2, 2020

(51) Int. Cl.
C07C 255/54 (2006.01)
C07F 3/06 (2006.01)
A61P 35/00 (2006.01)

(52) U.S. Cl.
CPC ............ *C07C 255/54* (2013.01); *A61P 35/00* (2018.01); *C07F 3/06* (2013.01)

(58) Field of Classification Search
CPC ............ A61K 41/0095; A61K 41/0071; C07C 255/54; C07C 317/18; C07D 487/22; C07F 5/069; C07F 7/025; C09B 47/045; C09B 47/067; C09B 47/08
USPC .......................................................... 514/185
See application file for complete search history.

(56) References Cited

U.S. PATENT DOCUMENTS

| | | | |
|---|---|---|---|
| 5,401,100 A * | 3/1995 | Thackston | B65D 75/30 206/306 |
| 5,466,468 A * | 11/1995 | Schneider | A61K 9/127 424/450 |
| 5,486,274 A | 1/1996 | Thetford et al. | |
| 5,616,342 A * | 4/1997 | Lyons | A61K 9/1075 424/450 |
| 5,616,602 A * | 4/1997 | Taylor | A61K 9/0014 424/450 |
| 5,723,148 A * | 3/1998 | Love | A61K 9/0014 424/450 |
| 7,842,682 B2 | 11/2010 | Roncucci et al. | |
| 8,524,891 B2 | 9/2013 | Hammer et al. | |
| 9,006,428 B2 | 4/2015 | Kim et al. | |

OTHER PUBLICATIONS

Oskan Soyer Can et al. (Inorganica Chimica Acta, 465 (2017) 31-37).*
McKeown et al., "A Phthalocyanine Clathrate of Cubic Symmetry Containing Interconnected Solvent-Filled Voids of Nanometer Dimensions," Angewandte Chemie: International Edition, 44:46, 2005, 7546-7549.
Nemykin et al., "Synthesis of Substituted Phthalocyanines," ARKIVOC, 2010, 136-208.
D'Mwanza et al., "Exploiting Click Chemistry for the Covalent Immobilization of Tetra (4-Propargyloxyphenoxy) Metallophthalocyanines onto Phenylazide-Grafted Gold Surfaces," Electrochirnica Acta 254, 2017, 89-100.
D'Mwanza et al., "The Effect of the Cobalt and Manganese Central Metal Ions on the Nonlinear Optical Properties of Tetra(4-Propargyloxyphenoxy)Phthalocyanines," New Journal of Chemistry, 42(12) 2018.
Wohrle, et al., "Synthesis and Photochemical Properties of Phthalocyanine Zinc (II) Complexes Containing O-Carborane Units," Journal of Organometallic Chemistry, 747, 2013, 98-105.
Mwanza, et al., "Tetra (4-propargyloxyphenoxy) Phthalocyanines: Facile Synthesis, Fluorescence and Thermal Properties," 134, 2017, 263-274.

* cited by examiner

*Primary Examiner* — Sabiha N Qazi
(74) *Attorney, Agent, or Firm* — Richard C. Litman; Nath, Goldberg & Meyer

(57) ABSTRACT

Propargyl-functionalized macrocyclic compounds can include non-aggregating compounds having at least one phthalocyanine (Pc), azaphthalocyanine (AzaPc), or naphthalocyanine (Nc) unit. The compounds can be metal-free or metal-complexed. The metal-complexed compounds can include zinc (II), for example. The compounds can include multiple propargyl moieties at different sites, e.g., peripheral or non-peripheral sites, as described herein. Exemplary compounds include an azaphthalocyanine complex (AzaPc1) and phthalocyanine complexes (Pc2-Pc5). The compounds may provide efficient solubility in aqueous and/or organic solvents, optimal physicochemical properties, improved photo-sensitizability, significant tumor specificity, and electron transfer tunability. The compounds can provide suitable non-aggregated molecular scaffolds for construction of numerous macrocycle derivatives via different organic transformation methodologies, e.g., Cu(I)-catalyzed azide-alkyne cycloaddition (CuAAC).

2 Claims, 16 Drawing Sheets

= propargyl   Y = N or CH   M = Zn

= propargyl   R = H or Cl   M = Zn

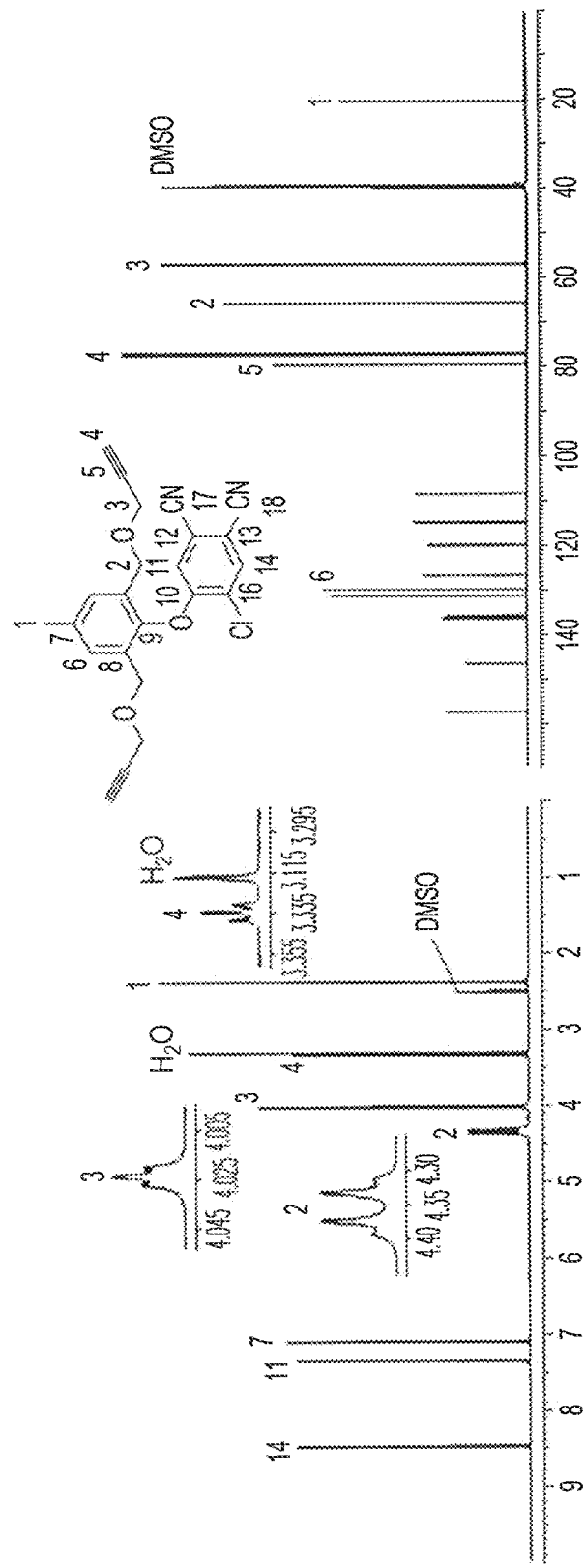

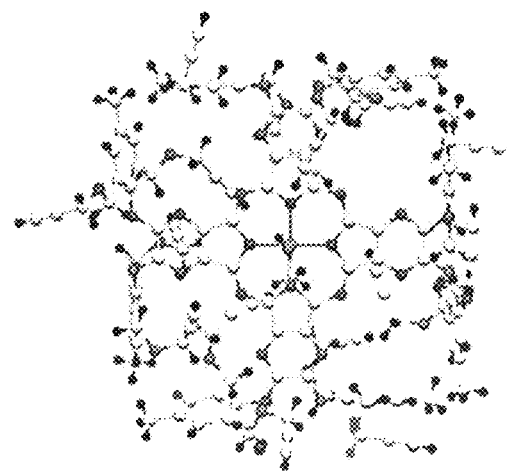
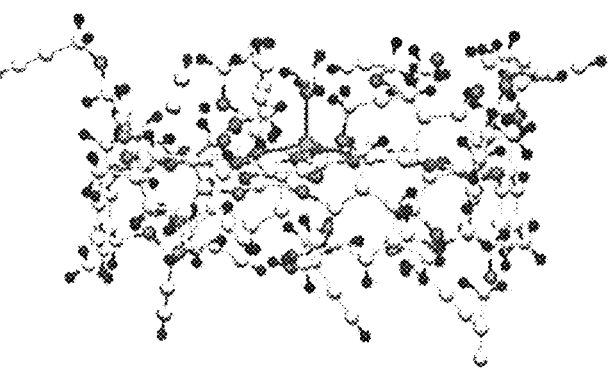
AzaPc1
FIG. 8A
AzaPc1
FIG. 8B
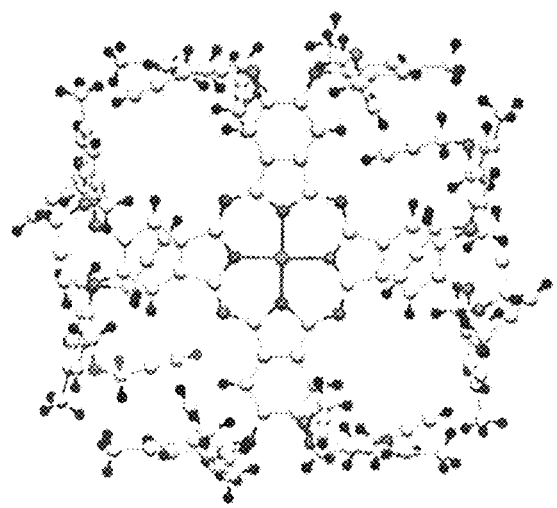
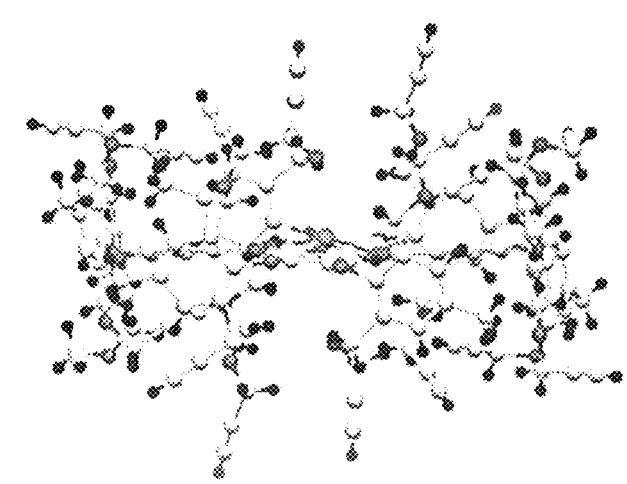
Pc2
FIG. 9A
Pc2
FIG. 9B

PROPARGYL-FUNCTIONALIZED MACROCYCLIC COMPOUNDS

BACKGROUND

1. Field

The disclosure of the present patent application relates to phthalocyanine derivatives, and particularly to azaphthalocyanine, naphthalocyanine, and phthalocyanine derivatives functionalized with propargyl containing moieties, methods of forming such derivatives and precursors for such derivatives.

2. Description of the Related Art

Derivatives of phthalocyanine (Pc) or Pc-analogs—e.g., azaphthalocyanine (AzaPc) or naphthalocyanine (Nc)—require a proper conjugation of suitable substituents that are capable of providing unique characteristics, properties and/or physiochemical features necessary for particular applications. Prior synthetic procedures for generating functionalized macrocycles usually have numerous drawbacks, including low yield, difficult purifications, interference between the substituents with harsh reaction conditions during cyclization, and undesired side products.

Thus, propargyl functionalized macrocyclic compounds solving the aforementioned problems are desired.

SUMMARY

Propargyl-functionalized macrocyclic compounds can include non-aggregating compounds having at least one phthalocyanine (Pc), azaphthalocyanine (AzaPc), or naphthalocyanine (Nc) unit. The compounds can be metal-free or metal-complexed. The metal-complexed compounds can include zinc (II), for example. The compounds can include multiple propargyl moieties at different sites, e.g., peripheral or non-peripheral sites, as described herein. Exemplary compounds include an azaphthalocyanine complex (AzaPc1) and phthalocyanine complexes (Pc2-Pc5). The compounds may provide efficient solubility in aqueous and/or organic solvents, optimal physicochemical properties, improved photo-sensitizability, significant tumor specificity, and electron transfer tenability upon further modification. The compounds can provide suitable non-aggregated molecular scaffolds for construction of numerous macrocycle derivatives via different organic transformation methodologies, e.g., Cu(I)-catalyzed azide-alkyne cycloaddition (CuAAC).

These and other features of the present disclosure will become readily apparent upon further review of the following specification and drawings.

BRIEF DESCRIPTION OF THE DRAWINGS

FIGS. 4A-4B show the $^1$H-NMR and $^{13}$C-NMR spectra, respectively, of di-propargyl Pc-precursor 5.

FIGS. 8A-8B show the crystal structure of AzaPc1; (8A) top view and (8B) side view.

FIGS. 9A-9B show the crystal structure of Pc2 (9A) top view and (9B) side view (due to positional disorder, the Zn(II) ion in this crystal is observed as occupying both sides of the Pc plane with half occupancies; however, one such Zn(II) is hidden in this figure, for clarity).

(FIG. 13A) $^1$H-NMR spectrum at 25° C.; (FIG. 13B) $^1$H-NMR spectrum at 95° C.; (FIG. 13C) $^{13}$C-NMR spectrum at 25° C.

Similar reference characters denote corresponding features consistently throughout the attached drawings.

DETAILED DESCRIPTION OF THE PREFERRED EMBODIMENTS

Propargyl-functionalized macrocyclic compounds can include compounds having the following general formula (I):

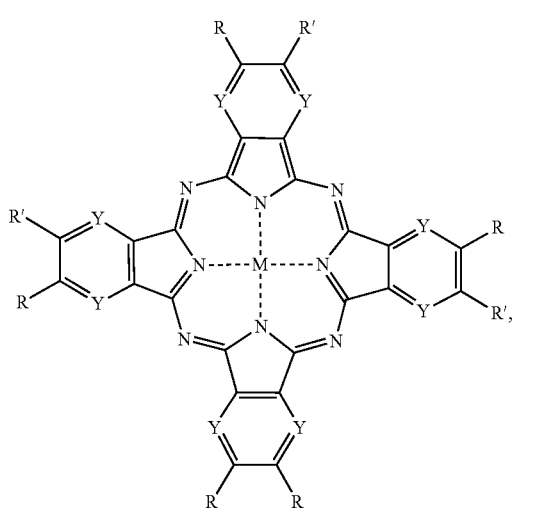

Formula I wherein M is a metal cation;
wherein Y is selected from the group consisting of N and CR", and Y' is selected from the group consisting of N and CR'";
wherein R, R', R", and R'" are independently selected from the group consisting of H, X, halogen, alkyl, aryl, substituted alkyl, substituted aryl, alcohol, amine, and carboxylic acid; and
wherein X is

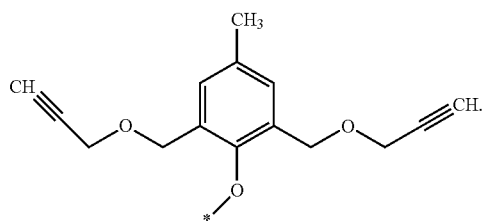 [SMILES: *Oc1c(COCC#C)cc(C)cc1COCC#C]

According to an embodiment, the propargyl-functionalized macrocyclic compounds comprise one or more compounds selected from the group consisting of:

AzaPc1

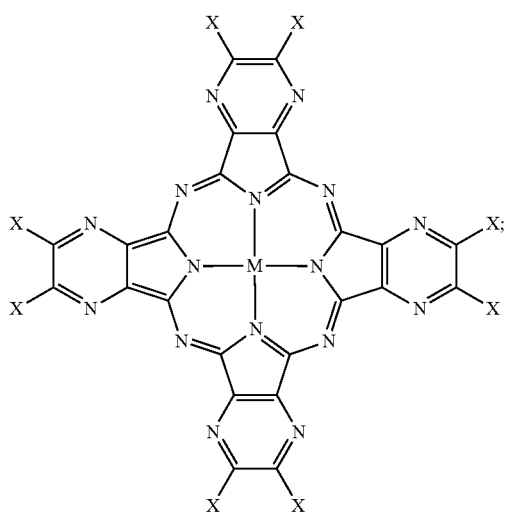

Pc2

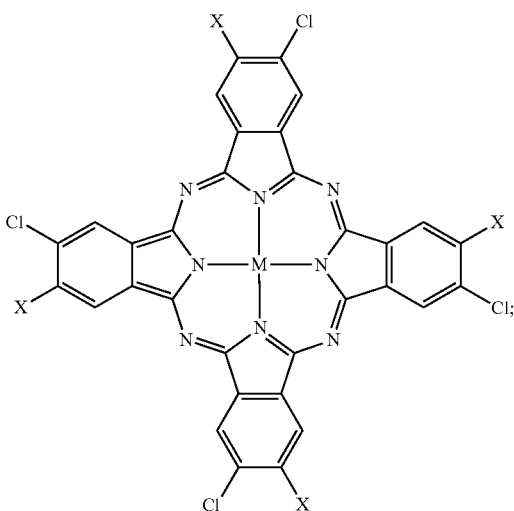

Pc3

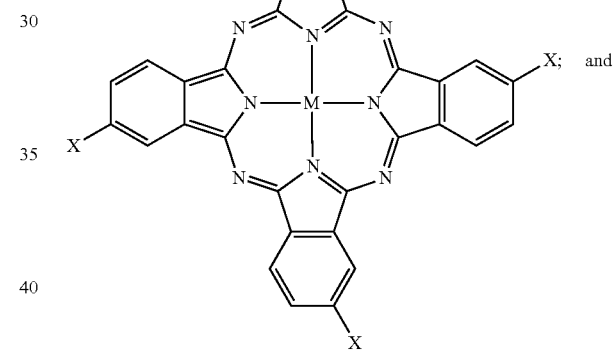

Pc4 and

Pc5

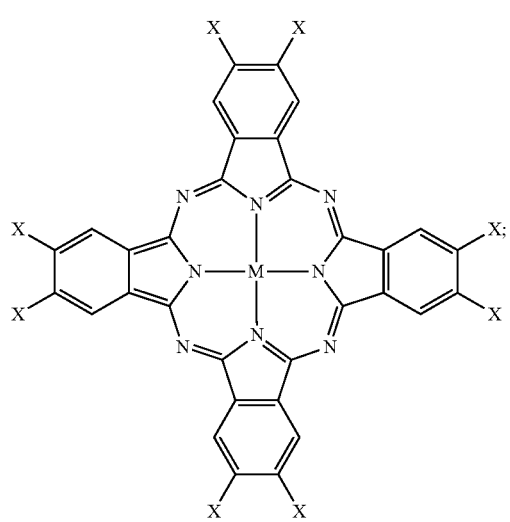

The compounds can include a backbone skeleton including phthalocyanine (Pc) or a pthalocyanine analog (Pc-analog). The Pc-analog can include, for example, azaphthalocyanine (AzaPc) or naphthalocyanine (Nc). The compounds include orthogonal bulky phenoxyl substituents on the Pc or Pc-analog backbone structures and multiple propargyl units at peripheral and/or non-peripheral sites. The orthogonal bulky phenoxyl substituents prevent self-association between the macrocyclic cores. The multiple propargyl or alkyne units are highly reactive to various reaction conditions and chemical transformations.

Figure 1A:
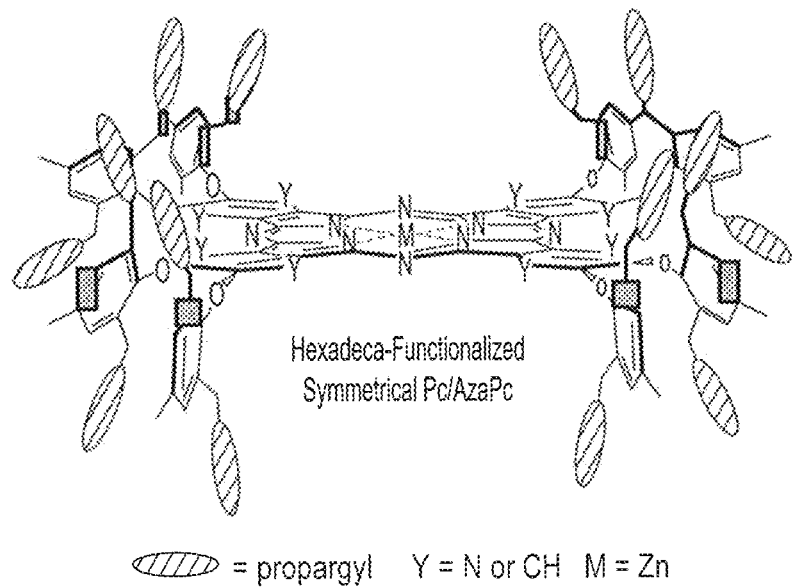
FIGS. 1A-1B show general structures of hexadeca- and octa-propargyl containing zinc (II) Pc/AzaPc complexes according to embodiments of the present disclosure.
Figure 1B:
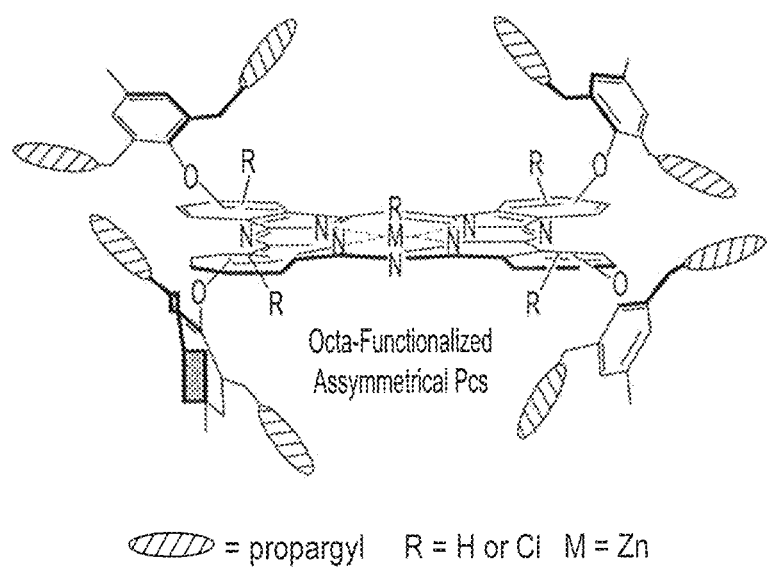

The compounds include multiple propargyl moieties based on phenoxyl units that lie perpendicular or almost perpendicular to the cyclic planar Pc or Pc-analog cores (FIGS. 1A-1B). The exemplary compounds AzaPc1 and Pc2 are hexadeca-functionalized, symmetric compounds. The exemplary compounds Pc3-Pc5 are octa-functionalized (positional isomer) compounds. Bulky phenoxyl groups at various peripheral/non-peripheral sites on the Pc/Pc-analogs impose steric hindrance to any possible self-association between the planar conjugated systems. Thus, no H- or J-type π-π stacking between the macrocyclic molecules can occur in dissolved conditions and the compounds can remain in non-aggregated form.

Terminal alkynes represent an important class of functionality that is widely applied in numerous organic transformation reactions, such as the click reaction; Cu(I)-catalyzed azide-alkyne cycloaddition (CuAAC); Pd(0)-catalyzed Sonogashira; Cu(I)-catalyzed Eglinton; Cu(II)-catalyzed Glaser-Hay; Cu(I)-catalyzed Cadiot-Chodkiewicz cross-coupling; thiol-yne coupling reactions; and others. Among these organic transformation approaches, the CuAAC reaction is particularly significant in various research areas. The simple setup and workup, the use of benign or easily removed solvents and low-cost Cu-catalyst, fast reaction rates, simple targeted compound isolation and high yield of the desired product are major advantages of using this type of 1,3-cycloaddition reaction. The highly stable resulting 1,4-disubstituted 1,2,3-triazole linkages can be further modified to their corresponding salts, i.e., 1,2,3-triazolium salt, which can be used advantageously for synthesis of the water-soluble Pc/Pc-analog compounds.

Thus, the presence and fixed orientation of the multiple propargyl units of the present macrocyclic compounds are significant. The present compounds provide suitable non-aggregated molecular scaffolds for attaching, directing and/or orienting valuable sets of ligands and/or groups, e.g., via CuAAC. The compounds can be soluble in aqueous and/or organic solvents upon further modification by conjugating with water-soluble substrates, such as carbohydrates, amino acids, and peptides. The compounds have optimum physicochemical properties, improved photo-sensitizability, significant tumor specificity, and electron transfer tenability. The compounds can provide ready-made, non-aggregated macrocyclic materials suitable for use as starting platforms for achieving various macrocyclic derivatives useful in a variety of research applications as described herein. Additionally, the dual spatial directionality of the terminal ethynyl ends of the compounds can provide pseudo-cavities, which are particularly useful for applications such as host-guest chemistry, catalysis, and drug delivery. The compounds can be used as starting platforms for constructing macrocyclic derivative compounds including alkyl groups, aryl groups, saccharides, amino acids, nucleic acids, drugs, biomarkers, cyclodextrins (CDs), biotin, folic acid, proteins, polymers, vitamins, photosensors and many others which can be easily prepared in gram quantities for various valuable applications. The compounds or their corresponding macrocyclic derivative compounds can be used in many research areas, including, for example, solar-cells, liquid crystals, photovoltaics, chemical or biological sensors, photodynamic therapy (PDT), ionic liquids (ILs), catalysis, bioconjugation, drug delivery or discovery, polymer and material science, supramolecular chemistry, host-guest chemistry, optical light emitting diode (OLED), and MRI agents.

As described in detail herein, the present compounds (upon attachment to carbohydrates or other suitable cancer-binding moieties) are suitable for use as photosensitizers for cancer treatment by photodynamic therapy method due to their high singlet oxygen production abilities. According to an embodiment, a method of killing cancer cells can include contacting a target cancer cell with one or more of the propargyl-functionalized macrocyclic compounds described herein, and subjecting the target cancer cell to light irradiation while the compound is contacting the target cancer cell to kill the target cancer cell.

As described in detail herein, synthesis of the present compounds includes two major steps. The first synthetic step includes decorating activated pyrazine/phthalonitrile substrates with dipropargyl-containing p-cresol substituents for the synthesis of tetra- and di-propargyl functionalized precursors 3-7. The second synthetic step includes subjecting the resulting precursors to metallo-cyclotetramerization reactions to produce the present compounds, for example, AzaPc1 and Pc2-Pc5.

As set forth herein, precursors 3-7 can be synthesized by reacting pyrazine/phthalonitrile substrates with dipropargyl-containing p-cresol substituents. It should be understood, however, that other compounds can be used for synthesizing terminal ethynyl precursors. Exemplary aromatic nucleophile substrates including different halogenated moieties and/or good leaving groups that can be used for synthesis of terminal ethynyl precursors are provided below:

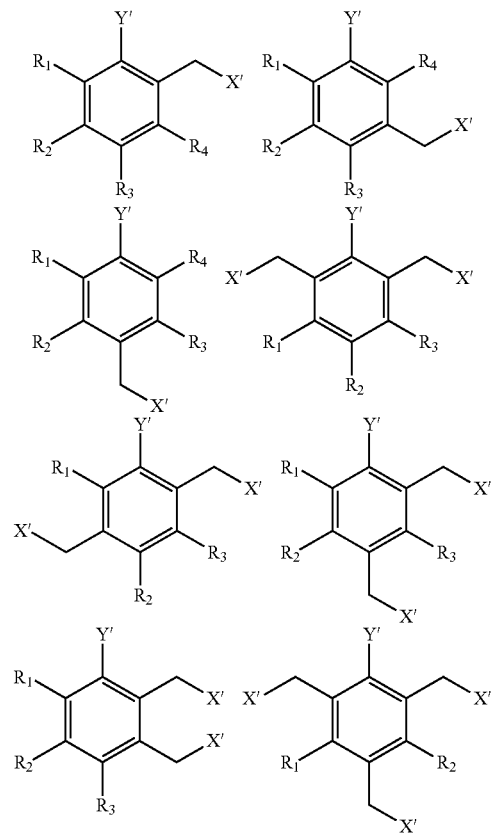

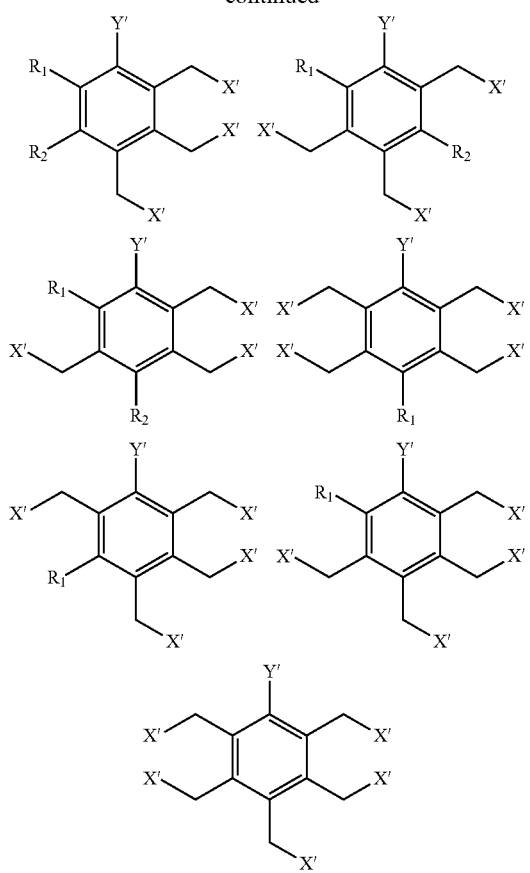

Y' = OH, NH₂, SH, SeH, or PH₂.
X' = any possible halogen and/or any possible good leaving group.
R₁, R₂, R₃, R₄ = H and/or any possible alkyl and/or aryl and/or halogen.

Other terminal ethynyl substrates, including di and tri-terminal ethynyl substrates, can be prepared using conventional methods. Propargyl derivatives can be introduced on the halogenated and/or good leaving groups containing aromatic phenols, amines, thiols, etc. for the synthesis of propargyl modified substrates, as shown below:

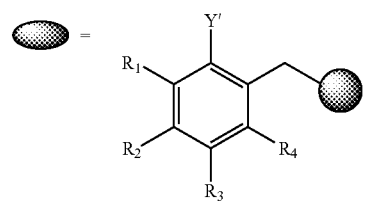

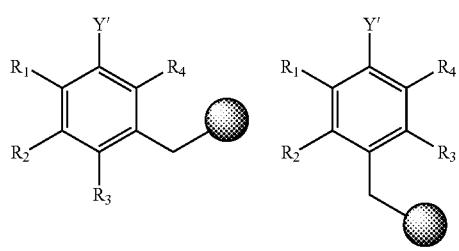

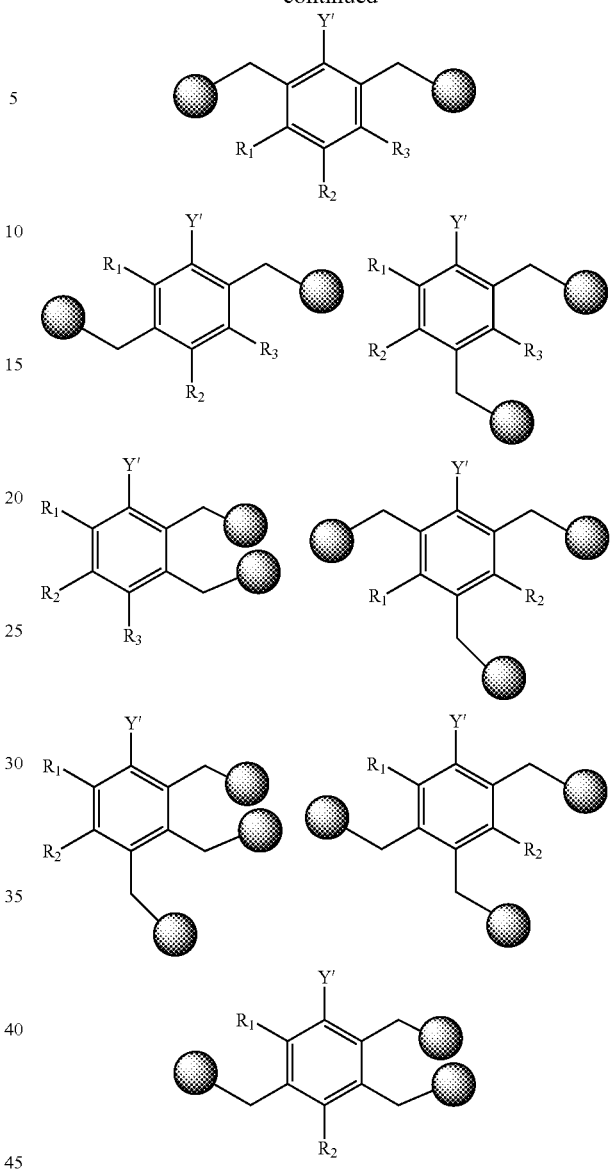

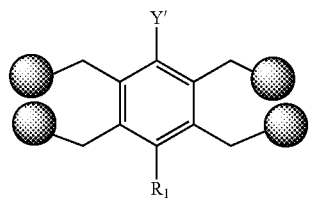

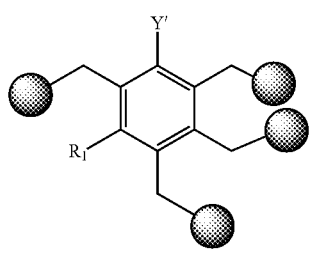

-continued

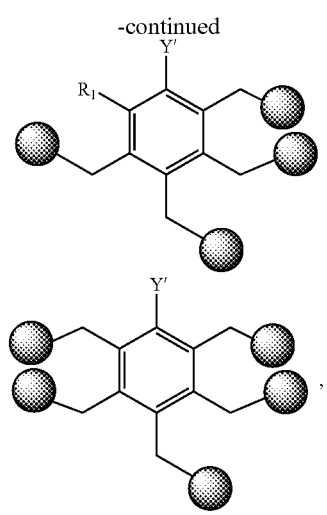

where

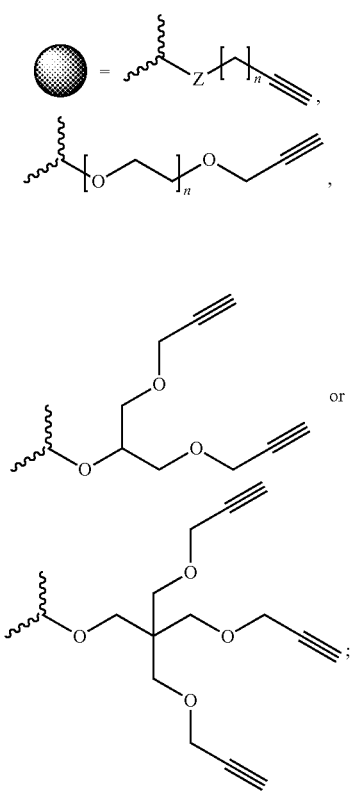

Y = OH, NH₂, SH, SeH, PH₂;
Z = O, NH, S, Se, PH;
n = any possible number; and
R₁, R₂, R₃, R₄, R₅, R₆, R₇, R₈ = H and/or any possible alkyl and/or aryl and/or halogen Aromatic di-nucleophile substrates can also be applied for the preparation of mono-propargyl aromatic derivatives upon modifying only one nucleophilic site with a propargyl group.

Any of the propargyl-modified substrates described above can be used for synthesizing precursor compounds according to the present teachings following the synthesis methods described for precursors 3-7.

The present propargyl-functionalized macrocyclic compounds can provide ready-made, non-aggregated macrocyclic materials suitable for use as starting platforms for achieving various macrocyclic derivatives useful in a variety of research applications. For example, an organic transformation reaction, such as the Cu(I)-catalyzed azide-alkyne cycloaddition (CuAAC), the Pd(0)-catalyzed Sonogashira cross-coupling, the Cu(I)-catalyzed Eglinton cross-coupling, Cu(I)-catalyzed Glaser-Hay cross-coupling, Cu(I)-catalyzed Cadiot-Chodkiewiez cross-coupling, thiol-yne, can be used for synthesizing valuable macrocyclic derivatives from the present compounds. For example, the transformation reaction can be used to add polyethylene glycols (PEGs) on the Pc/AzaPc/Nc cyclic backbones for the synthesis of water-soluble PEG systems via CuAAC. The presence of multiple PEGs would play a major role keeping the Pc/Pc-analogy cores away from each other.

The transformation reaction can be used to introduce various vitamins including; A, B, C, D, E and K on the present compounds and the resulting assemblies can be used in biological studies. Among all vitamins, L-ascorbic acid (vitamin C) has been widely applied in many organic syntheses, specifically, in the field of catalysis. The unique structural properties of the water-soluble L-ascorbic acid salted version, i.e.; Na-L-ascorbate, raise its advantages as an efficient reducing agent and radical initiator in aqueous media. Thus, combining such moiety on the macrocyclic skeletons would be noteworthy since the resulting structures would be water-soluble and the orientation (spatial directionality) of the L-ascorbic acid units with respect to the cyclic cores would provide active sites i.e.; pseudo-microreactors on both rims, capable to accommodate, catalyze and/or radical-initiate different organic transformations in an aqueous environment, especially, for water-insoluble organic substrates. In addition, L-ascorbic acid has been used in the formation of metal nanoparticles. Therefore, the presence of multiple L-ascorbic acids on both rims (top/bottom), their orientation with respect to the planar macrocyclic cores, their spatial directionality, and varying the linkages between the multi-L-ascorbic acid units on the cyclic skeletons, would play a significant role in the synthesis of sizable (selective sizes) metal nanoparticles (e.g. gold nanoparticles). Moreover, an MRI contrast agent such as Gd-DOTA (1,4,7,10-tetra-azacyclododecane-1,4,7,10-tetraacetic acid) based on the present compounds, e.g., AzaPc1 via CuAAC, can potentially be useful as a theragnostic agent.

In the field of carbohydrates, many sugars including mono-, di-, oligo- or polysaccharides can be conjugated on the present compounds via the reactions described. The existence of multiple saccharides on the macrocyclic structures would enhance the solubility of the compounds in aqueous systems. Also, many applications can be evaluated for these glyco-Pcs/Pc-analogs, including; biological activities, cell-cell and cell-virus recognition, cell adhesion and others. Additionally, the orientation and/or the spatial directionality of the sugar unit on the macrocyclic structures would provide pseudo-saccharide active sites on both rims which can be used to catalyze, enhance and improve different organic reactions in aqueous media, especially, for water-insoluble organic species. Cyclodextrins (CDs) are macromolecules composed of glycopyranose monomer units connected to each other in a cyclic-type of structure through the α-(1,4) bond. The most common and known CDs are the α, β and γ which consist of six, seven and eight, respectively. Introducing CDs on the macrocyclic backbones can be accomplished using any of the organic methodologies mentioned above. For example, the CuAAC reaction can be used to create an assembly including multiple β-CD based on AzaPc1. The resulting CD-Pcs/AzaPcs/Ncs can be applied as host-guest systems. The CD molecular units can encapsulate various water-insoluble organic substrates within their cavities and thereby enhance their dissolution in aqueous environment. These assemblies can also be used in separation chemistry, chiral recognition, catalysis along with molecular bio-sensing.

In addition, amino acids based on Pc/AzaPc/Nc macrocycles can be obtained using the organic methodologies mentioned above. Amino acids based on the present macrocyclic systems can act as chiral-vessels to catalyze chiral reactions in water. Also, they can form supramolecular assemblies in water such as nanotubes, polymer and other structures, via donor/acceptor H-bonding between the amino and carboxylate ions or through metal-complexation in the presence of suitable metals. Likewise, many customized polymeric amino acids, i.e.; homo-, co-, block and/or random peptides or proteins can be attached on the present macrocyclic scaffolds using any of the organic procedures mentioned. The resulting peptido-Pc/AaPc/Nc materials can function as recoverable and reusable catalysts in water or as water-soluble peptides that can be influenced by varying the pH-value in the formation of secondary supramolecular assemblies, i.e.; random-coil, β-sheet or α-helical structures. Also, the peptide-Pcs/Pc-analogs such as L-glutamic acid or L-lysine, can be applied in the field of drug delivery since the resulting structures would undergo encapsulation/releasing processes in green solvent, water, at different pH-values.

Furthermore, to improve photophysical and photochemical features, different compounds, namely; anthracene, pyrene, perylene, bodipy, proflavine, coumarin, subphthalocyanine, C60, carbazole and many others can be coupled on the Pc/AzaPc/Nc skeletons described herein by applying any of the methodologies provided above. Furthermore, to improve the photophysical and photochemical features, different sets of compounds, namely; anthracene, pyrene, perylene, bodipy, proflavine, coumarin, subphthalocyanine, C60, carbazole and many others can be coupled on the Pc/AzaPc/Nc skeletons described herein by applying any of the methodologies provided above.

Such molecular assemblies, for example; pyrene-AzaPc, can bind on either graphene or carbon nanotube surfaces via multiple π-π interactions. The obtained structures can be applied in the field of electrochemistry and other research areas as well.

Moreover, numerous types of drugs, such as doxorubicin, deoxyribonuleosides, erlotinib, zidovudine and others can be joined on the macrocyclic assemblies via any synthetic procedure claimed previously. These drug-based Pcs/AzaPcs/Ncs can be used as smart photosensors for synergistic chemo-photodynamic therapy.

Consequently, morpholine can be easily linked on the Pc/AzaPc/Nc backbones via any of the methodologies described above. Morpholine can be converted into its salt simply by treating it with any appropriate counter ion which would improve the solubility of the overall morpholine Pc/Pc-analogy derivatives in water. Also, morpholine is widely applied as a building block for the construction of antibiotics (Linezolid), anticancer agents (Gefitinib), and analgesics (Dextromoramide).

Moreover, crown ether derivatives can be joined on the macrocyclic structures using any of the reactions previously described. For example; 15-crown-5 and diaza-18-crown-6 based on AzaPc1 system can be synthesized via CuAAC. Crown ethers bind to certain cations to form crown ether complexes that would be soluble in nonpolar environments. Thus, the photophysical and photochemical properties for such macro-systems can be tuned in organic solvents for sensing applications.

Moreover, any commercially available or synthetically prepared di-azido substrates, for example, alkyl or aryl di-azides, can be coupled on either the tetra- or di-alkyne macrocyclic-subunits via the CuAAC for the synthesis of rigid precursors. This would be monitored by a metallocyclization process for the construction of rigidified Pcs/Pc-analogs.

The present compounds, in their rigidified form, can be achieved by subjecting the terminal ethynyl containing Pc/AzaPc/Nc intermediates toward either the Cu(II)-catalyzed Glaser-Hay or Cu(I)-catalyzed Eglinton cross-coupling reactions. The obtained rigid precursors can then be applied as a starting material for assembling the macrocyclic systems via a metal-mediated cyclization process.

Additionally, many alkynide metal Pc/AzaPc/Nc complexes can be achieved upon linking different metals, namely; Cu, Ag, Li, Na, MgBr, $SiMe_3$ and others to the terminal ethynyl units. The existence of multiple metals might have a major influence on the photophysical and photochemical properties of the overall structures.

Likewise, the terminal alkyne moieties can be treated with $Co(CO_3)_8$ for the formation of Co containing Pc/AzaPc/Nc complexes. The resulting multiple Co complex based on the AzaPc1 assembly can be applied for the synthesis of cobalt nanoclusters. Further, double or triple decker Pc/AzaPc/Nc-based structures via metal complexation can be possibly obtained upon joining two or more macrocyclic molecules together using any suitable bridging metal ion. Moreover, ethynyl containing cyclic structures on the axial position can be afforded using silicon (Si) as the central atom. In addition, the terminal ethynyl units in the novel/proposed cyclic systems can be modified with halogens, namely; Br, I or Cl, upon their reactions with NBS, NIS or NCP, respectively. The presence of these halogens on the alkyne moieties can be used to enhance some organic reactions such as Cadiot-Chodkiewicz C-C coupling.

The present teachings are illustrated by the following examples.

EXAMPLES

All reactions were carried out under nitrogen atmosphere unless otherwise noted, all analyses were determined in Research Sector Projects Unit (RSPU) at Kuwait. TLC was performed using Polygram sil G/UV 254 TLC plates and visualization was carried out by ultraviolet lights at 254 nm and 350 nm. Column chromatography was performed using Merck silica gel 60 of mesh size 0.040-0.063 mm. $^1H$ and $^{13}C$ NMR spectra were recorded using Bruker DPX 600 at 600 MHz. IR spectra were obtained from Jasco 6300 FTIR. UV-Vis studies were achieved on a Varian Cary 5 spectrometer. Elemental analyses were carried out using Elementar-Vario Micro Cube. Exact Masses of unknown compounds were measured on GC-MS (Thermo). All of the studied compounds gave satisfactory elemental analyses with a difference that was less than 0.4% from the calculated values. In addition, the melting points were determined via differential scanning calorimetry (DSC) analyses on Shimadzu DSC-50.

All reagents were used with no further purification unless otherwise specified. 5,6-dichloropyrazine-2,3-dicarbonitrile and 4,5-dichlorophthalonitrile were purchased from Sigma-Aldrich chemical company. Anhydrous solvents were either supplied from Sigma-Aldrich or dried as described by Perrin. [D. D. Perrin, W. L. F. Armarego: Purification of laboratory chemicals, 3rd edn, Pergamon Press, Oxford, 1988.]

Example 1

Synthesis of Di-Propargyl p-Cresol 2

Initially, 2,6-bis(methylbromo)-p-cresol 1 was prepared in 51% yield according to the procedure described in Example 13 herein upon the reaction of 2,6-bis(methylhydroxyl)-p-cresol with 33% HBr in glacial acetic acid. As shown in the reaction scheme below, Compound 1 was then treated with propargyl alcohol for the synthesis of di-propargyl-p-cresol 2. The reaction was performed in dry tetrahydrofuran (THF) in the presence of NaH (60%) at 0° C. to room temperature, overnight to obtain the desired product 2 in 55% yield.

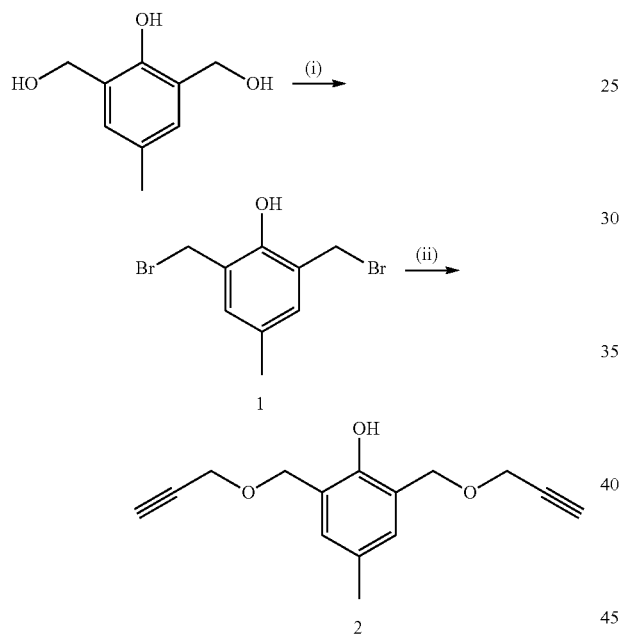

Figures 2A, 2B:
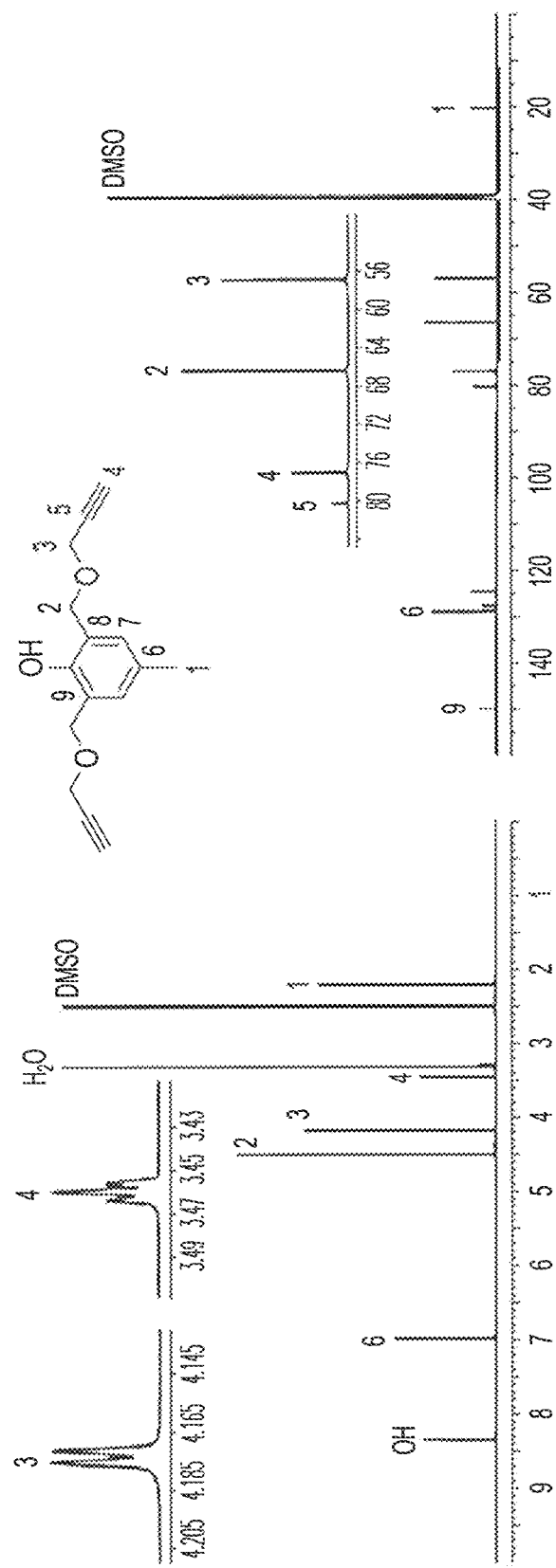
FIGS. 2A and 2B show the $^1$H- and $^{13}$C-NMR spectra, respectively, of cresol 2.
Figure 3A:
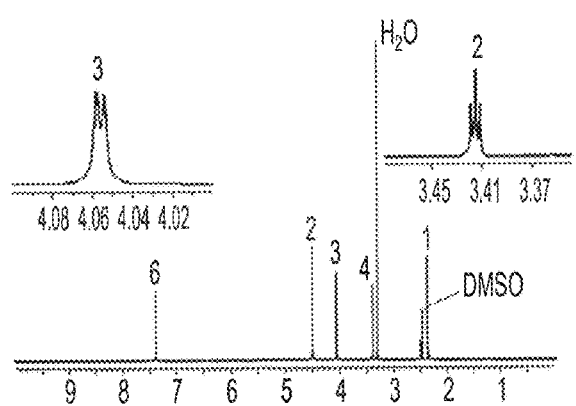
FIGS. 3A and 3C show the $^1$H-NMR spectra of tetra-propargyl AzaPc-precursor 3 and Pc-precursor 4, respectively.
Figure 3B:
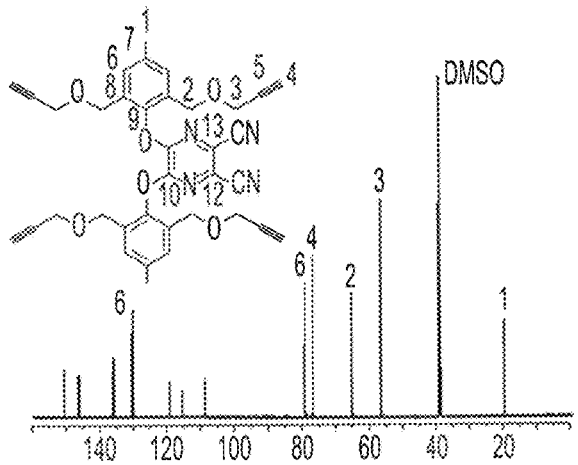
FIGS. 3B and 3D show $^{13}$C-NMR spectra of tetra-propargyl AzaPc-precursor 3 and Pc-precursor 4, respectively.
Figure 3C:
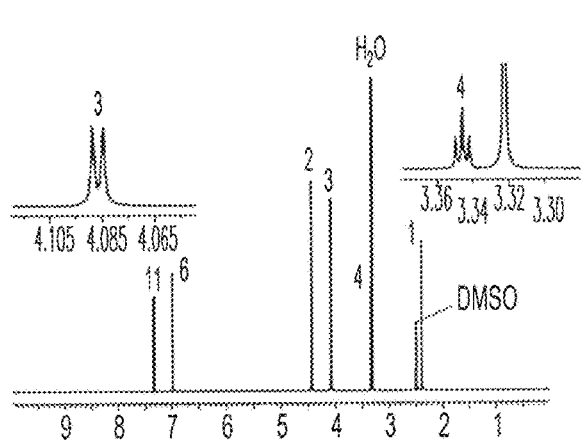
Figure 3D:
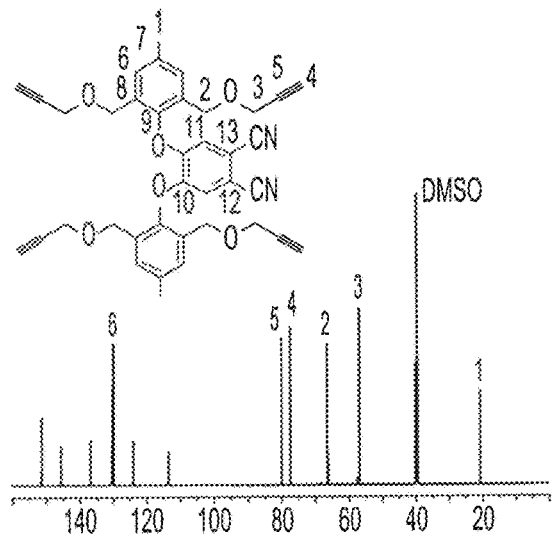

The novel cresol derivative 2 was fully characterized using NMR, HRMS and FT-IR spectral data and CHNX elemental analysis (FIGS. 2A-2B). In the $^1$H-NMR spectrum (600 MHz, DMSO-d$_6$, 25° C.) (FIG. 2A), the benzylic protons (—C$\underline{H}_3$, H1) were observed as a singlet at 2.20 ppm; terminal ethynyl protons (—C°C$\underline{H}$, H4) were observed as a triplet at 3.46 ppm with a J-value of 2.6 Hz; methyleneoxy protons (—CH$_2$OC$\underline{H}_2$CCH, H3) were observed as a doublet ppm (d, J=2.3 Hz) at 4.17 ppm; benzylic methylene protons (—C$\underline{H}_2$OCH$_2$CCH, H2) were observed as a singlet at 4.50 ppm; aromatic benzene (H7) was observed as singlets at 6.97 ppm; and phenolic protons (—O$\underline{H}$) were observed as 8.34 ppm. In the $^{13}$C-NMR spectrum (150 MHz, DMSO-d6, 25° C.) (FIG. 2B), ethynyl carbons (—C°$\underline{C}$H, C4) and (—$\underline{C}$°CH, C5) were observed at 77.2 ppm and 80.4 ppm, respectively, whereas the propargyl methylene carbons (—CH$_2$O$\underline{C}$H$_2$CCH, C3) were observed at 56.9 ppm. The benzylic methylene carbons (—$\underline{C}$H$_2$OCH$_2$CCH, C2) and the aromatic benzene carbons (C7) were at 66.5 ppm and 129.0 ppm, respectively. The HRMS (ESI-Q-TOF) for cresol 2 m/z (ESI-Q-TOF): observed 267.0985 (M+Na)+, calculated 267.0997 (M+Na)+ confirmed its chemical composition.

Example 2

Synthesis of Tetra- and Di-Propargyl Precursors 3-7

Cresol derivative 2 undergoes a nucleophilic substitution reaction for the synthesis of tetra-propargyl (3 and 4) and di-propargyl (5-7) precursors. As shown in the reaction schemes below and described in detail in Examples 14-17 herein, AzaPc-subunit 3 was obtained in gram quantity (97%) upon the reaction of compound 2 with 5,6-dichloro-2,3-dicyan-1,4-pyrazine in the presence of anhydrous K$_2$CO$_3$ in dry acetonitrile (25° C.) room temperature, overnight, while Pc-precursor 4 was obtained at a rate of 64% from the reaction of cresol derivative 2 with 4,5-dichlorophthalonitrile in the presence of anhydrous CsF in hot dry DMF (100° C. to room temperature, overnight).

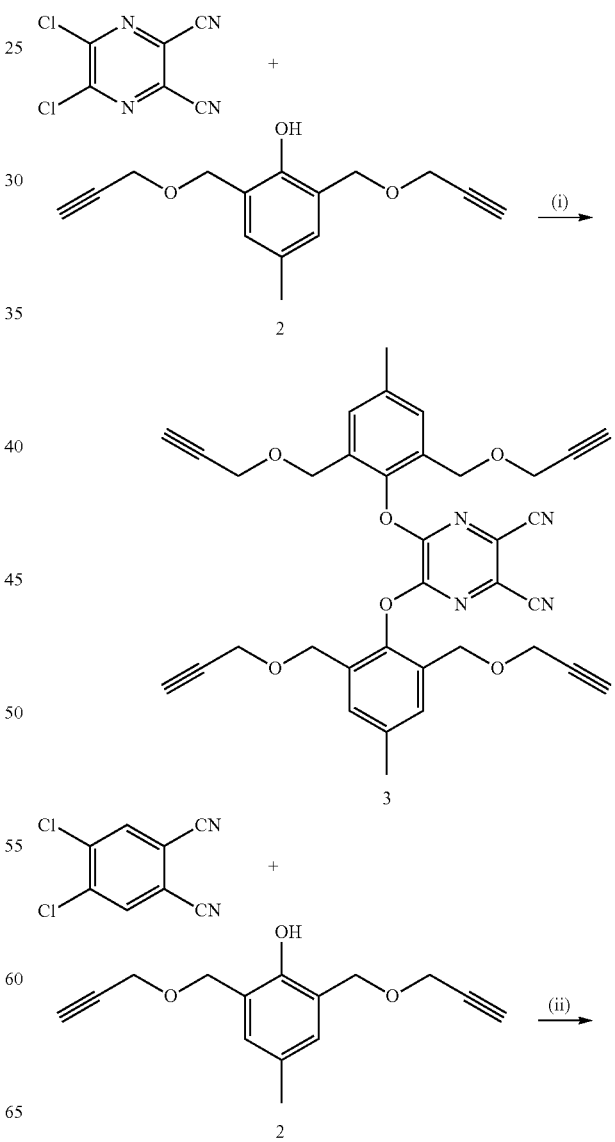

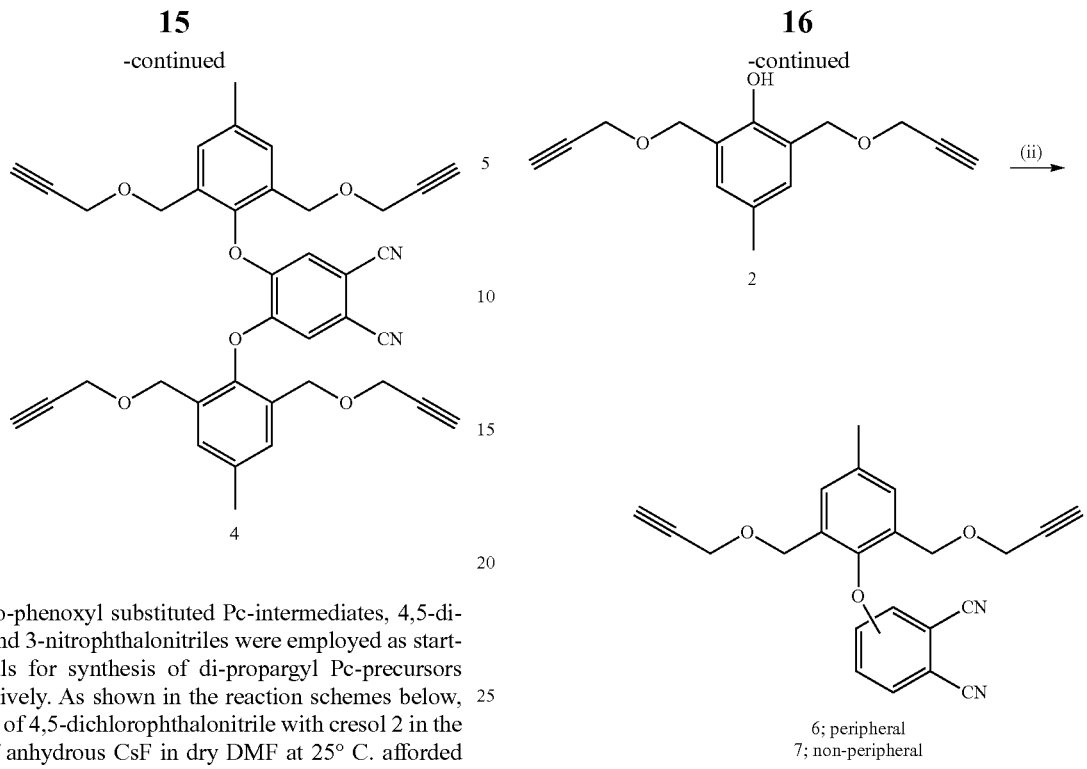

For mono-phenoxyl substituted Pc-intermediates, 4,5-dichloro, 4- and 3-nitrophthalonitriles were employed as starting materials for synthesis of di-propargyl Pc-precursors 5-7, respectively. As shown in the reaction schemes below, the reaction of 4,5-dichlorophthalonitrile with cresol 2 in the presence of anhydrous CsF in dry DMF at 25° C. afforded Pc-precursor 5 at high yields (85%), while the reaction of 4- and 3-nitrophthalonitriles with compound 2 in the presence of anhydrous CsF in dry DMF (100° C. to room temperature, overnight) resulted in non-peripheral structure 6 and peripheral structure 7 at yields of 89% and 85%, respectively.

Example 3

Synthesis of AzaPc1/Pc2-Pc5

As depicted in the reaction schemes below, all precursors 3-7 were subjected to zinc (II) mediated cyclotetramerization reactions for the construction of hexadeca- and octa-propargyl functionalized macrocyclic structures, AzaPc1 and Pc2-Pc5. All reactions were performed in dry pentanol in the presence of $Zn(OAc)_2$ and a catalytic amount of DMEA at high temperature (140° C.). The cyclization processes were carried out for 2-5 hours and resulted in formation of zinc (II) cyclic-tetramers in yields of 28-43%.

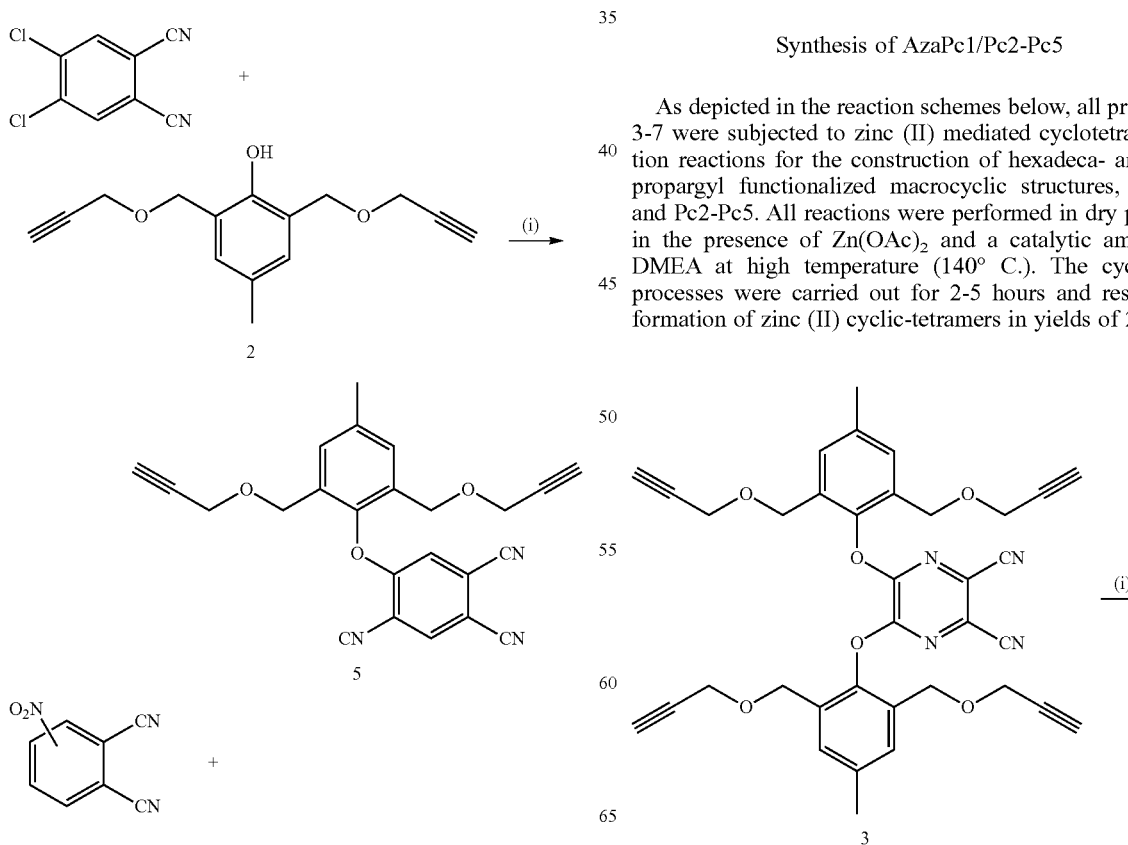

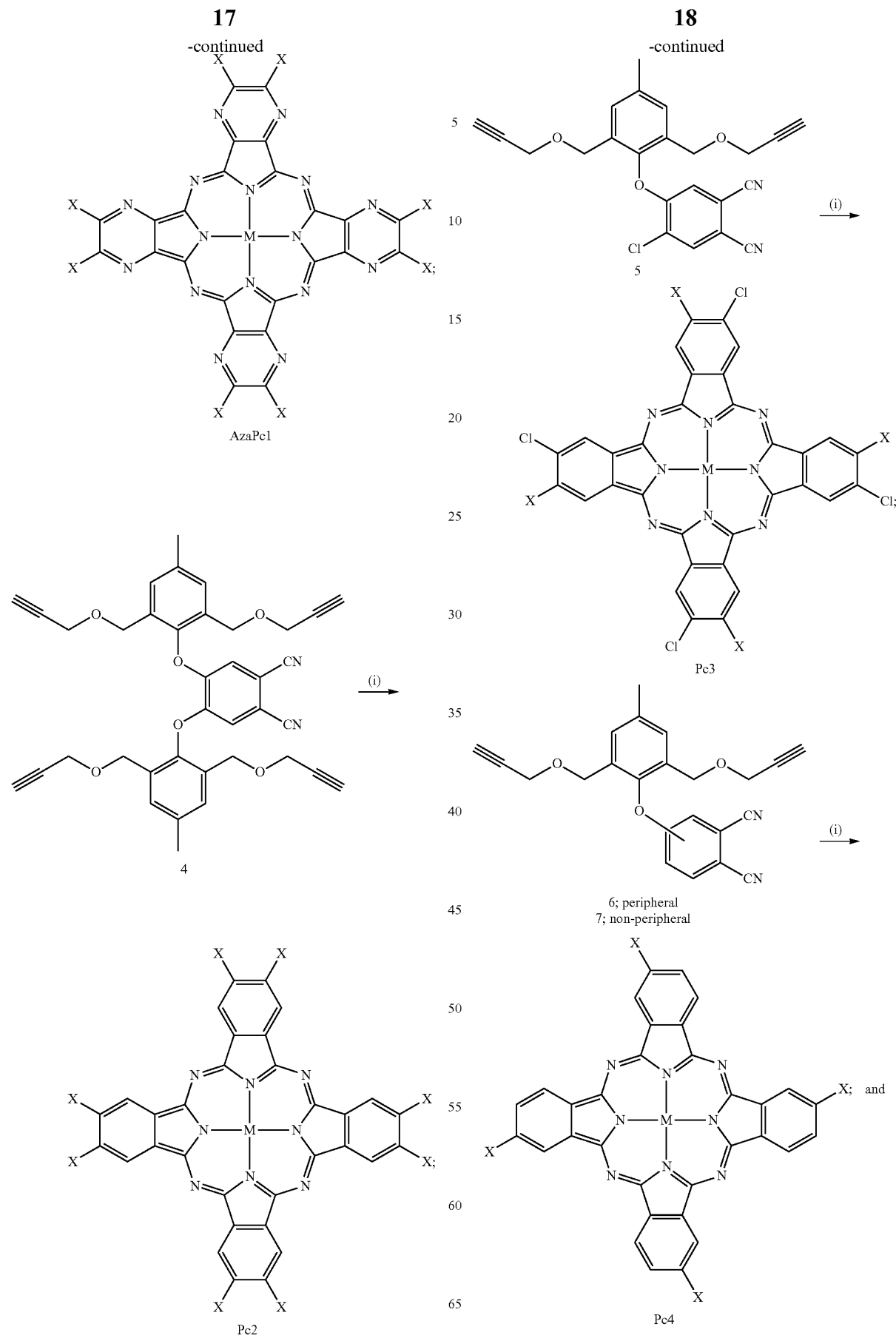

-continued

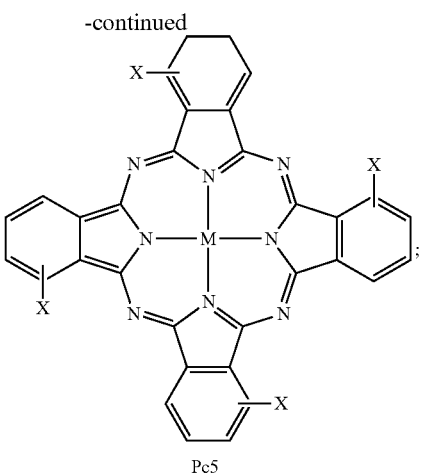

Pc5 where M is a Zn⁺ cation and X is

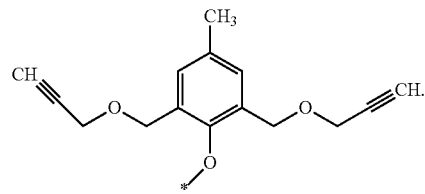

Example 4

Structural Analysis of Precursors 3-5

Evidence establishing the structures of compounds 3-5 by their respective NMR, HRMS, single crystal X-ray diffraction, FT-IR spectral data and CHNX elemental analysis are provided in FIGS. 3A-3D and FIGS. 4A-4B. The absence of the phenolic protons and the shift of the alkyne resonances in their $^1$H- and $^{13}$C-NMR spectra, are consistent with the expected structures of compounds 3-5. For example, in the $^1$H-NMR spectra (600 MHz, DMSO-d$_6$, 25° C.) of compounds 3 and 4 (FIGS. 3A-3B), the absence of phenolic resonance (OH) from 8.34 ppm (compared with FIG. 2A) and a shift of the benzylic protons (—CH$_3$, H1) from 2.20 ppm (compared with FIG. 2A) to 2.39 ppm were observed. The terminal ethynyl protons (—C° C.H, H4) in both precursors 3 and 4 appeared as triplets (t, J=2.6 Hz) at 3.42 ppm and 3.54 ppm, respectively, whereas the methyleneoxy protons (—CH$_2$OCH$_2$CCH, H3) appear shifted upfield from 4.17 ppm (compared with FIG. 2A) to 4.05 ppm in AzaPc-subunit 3 (d, J=2.3 Hz) and 4.08 ppm in Pc-subunit 4 (d, J=2.6 Hz). $^{13}$C-NMR spectra of precursors 3 and 4 (150 MHz, DMSO-d$_6$, 25° C.) (FIGS. 3C-3D), evince ethynyl carbons (—C°CH, C4) and (—C°CH, C5) appearing in the region of ~77.0 ppm and ~80.0 ppm, and propargyl methylene carbons (—CH$_2$OCH$_2$CCH, C3) around ~57.0 ppm. Similarly, the $^1$H-NMR spectrum (600 MHz, DMSO-d$_6$, 25° C.) of the mono-phenoxyl substituted intermediate 5 (FIG. 4A) shows the benzylic protons (H1) as a singlet at 2.38 ppm; the terminal alkyne protons (H4) as a triplet (t, J=2.3 Hz) at 3.33 ppm; methyleneoxy protons (H3) as a triplet at 4.02 (t, J=2.3 Hz); and benzylic methyleneoxy protons (H2) as a doublet of a doublet (dd, J=10.9, 35.0 Hz) at 4.32 ppm. The $^{13}$C-NMR spectrum or precursor 5 (150 MHz, DMSO-d$_6$, 25° C.) (FIG. 4B) evinces ethynyl carbons (C4) and (C5) at 77.2 ppm and 79.5 ppm, respectively, and propargyl methylene carbons (C3) at 57.7 ppm.

Figures 5A, 5B:
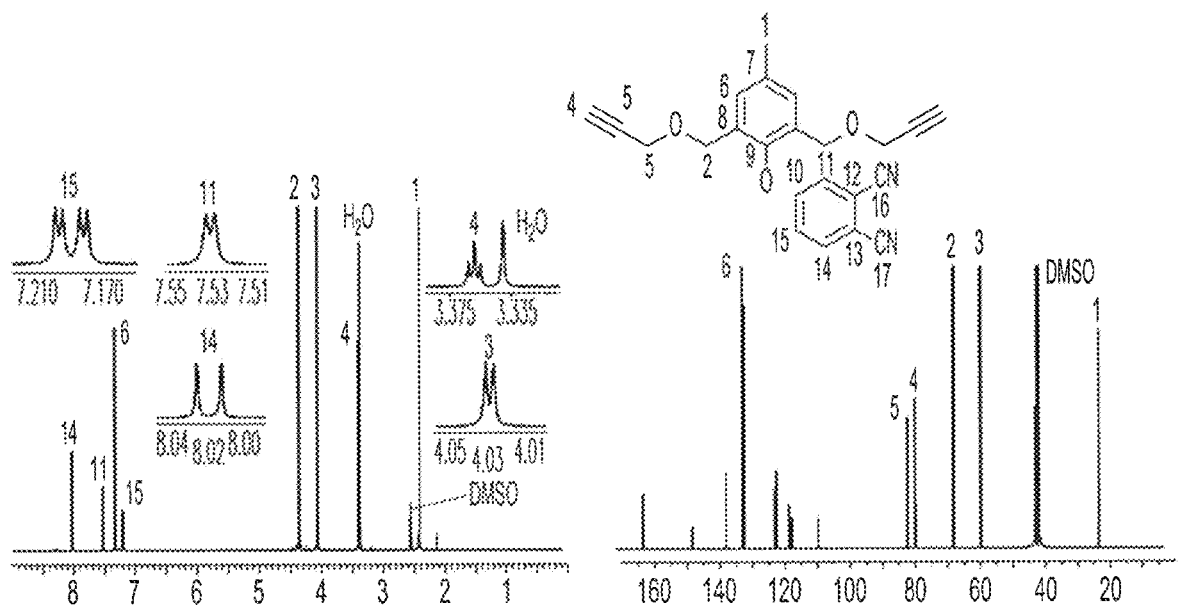
FIGS. 5A and 5C show the $^1$H-NMR spectra of di-propargyl Pc-precursors 6 and 7, respectively.
FIGS. 5B and 5D show the $^{13}$C-NMR spectra of di-propargyl Pc-precursors 6 and 7, respectively.
Figures 5C, 5D:
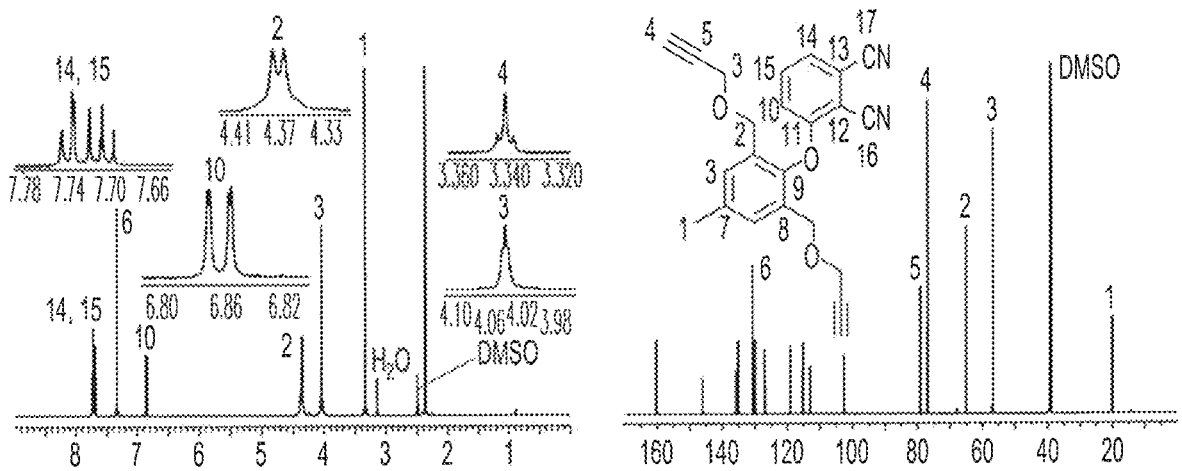

Moreover, the $^1$H-NMR spectra (600 MHz, DMSO-d$_6$, 25° C.) of the di-propargyl subunits 6 and 7 (FIGS. 5A and 5C), benzylic protons (H1) appear as a singlet at 2.37 ppm, ethynyl terminal protons (H4) appear as a triplet (t, J=2.3 Hz) at 3.34 ppm for precursor 6 and a triplet (t, J=2.3 Hz) at 3.33 ppm for subunit 7. Methyleneoxy protons (H3) appear as a triplet (t, J=2.6 Hz) at 4.03 ppm and a doublet (d, J=2.3 Hz) at 4.04 ppm, and benzylic methylenoxy protons (H2) appear as a singlet (4.33 ppm) and a doublet (d, J=9.0 Hz, 4.36 ppm) for Pc-precursor 6 and 7, respectively. $^{13}$C-NMR spectra (150 MHz, DMSO-d$_6$, 25° C.) (FIGS. 5B and 5D) show ethynyl carbons (C4) and (C5) at 77.3 ppm and around ~79.5-79.7 ppm and propargyl methylene carbons (C3) at 57.1 ppm in each of Pc-precursors 6 and 7.

The HRMS (ESI-Q-TOF) of all precursors show consistent results with the observed and expected chemical compositions as m/z (ESI-Q-TOF) values: observed 637.2037 (M+Na)+, calculated 637.2063 (M+Na)+ for AzaPc-precursor 3; observed 635.2122 (M+Na)+, calculated 635.2158 (M+Na)+ for Pc-precursor 4; observed 404.0922 (M)+, calculated 404.0928 (M)+ for Pc-precursor 5, observed 370.1312 (M)+, calculated 370.1317 (M)+ for Pc-precursor 6 and observed 370.1312 (M)+, calculated 370.1317 (M)+ for Pc-precursor 7.

Example 5

Crystal Structures of Precursors 3-7

Figure 6:
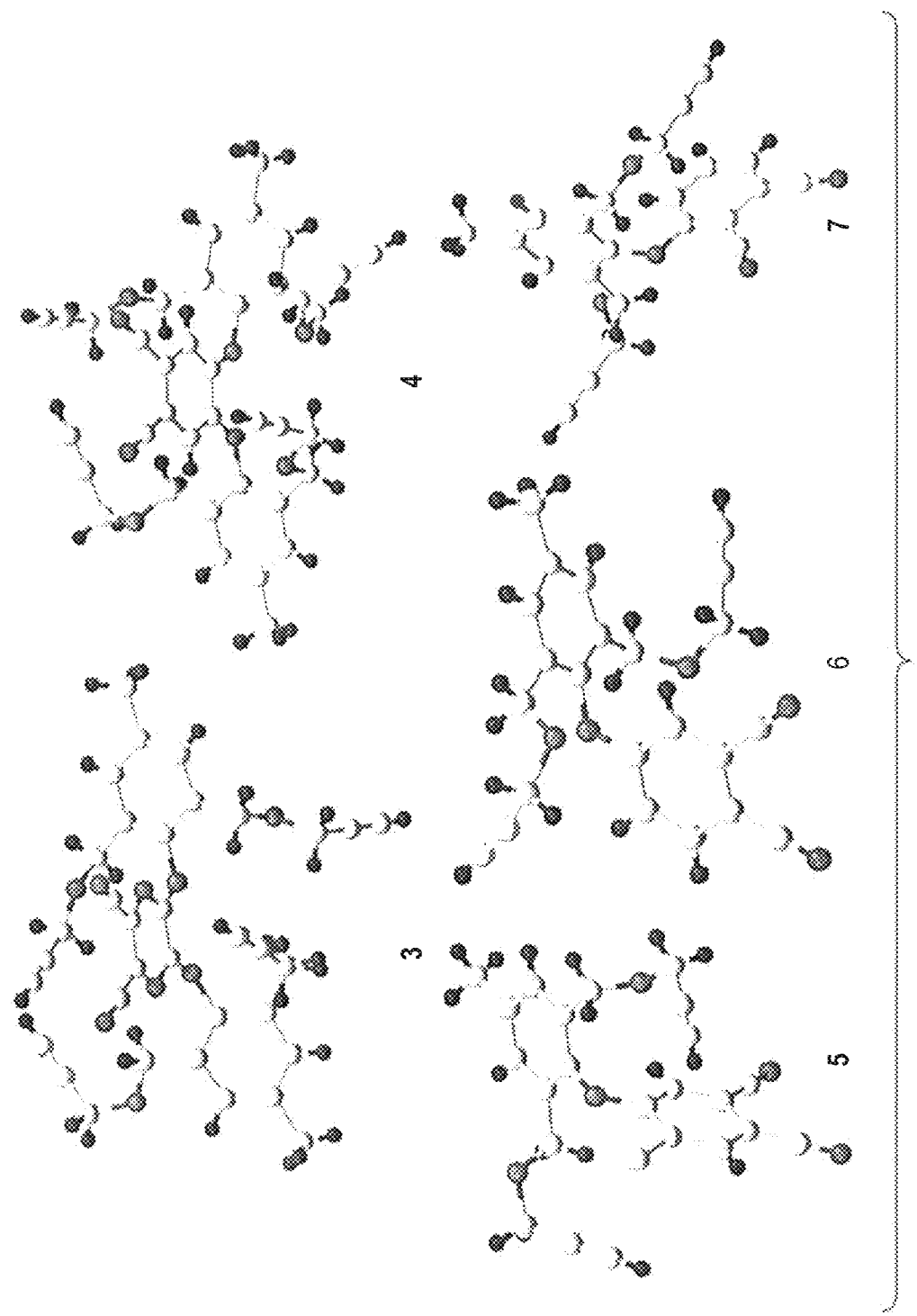
FIG. 6 shows crystal structure of tetra-propargyl precursors 3 and 4 and di-propargyl precursors 5-7 obtained from diffraction data.

Confirmation of the molecular features of all precursors 3-7 by single crystal X-ray diffraction analysis is shown in FIG. 6. The crystal structures provide valuable information regarding the orientation of the phenoxyl units and the propargyl moieties with respect to the pyrazine/phthalonitrile planes. The phenoxyl substituents are almost perpendicular to the planes of the pyrazine/phthalonitrile rings in all cases. This can be explained by the restricted rotation imposed on phenoxyl moieties by the ethynyl units. Such a blocked rotation caused by the propargyl chains is sufficient for ensuring the non-aggregating behavior of these monomers,

Example 6

Structural Analysis of AzaPc1 and Pc2-Pc5 by Elemental Analysis

Figure 7A:
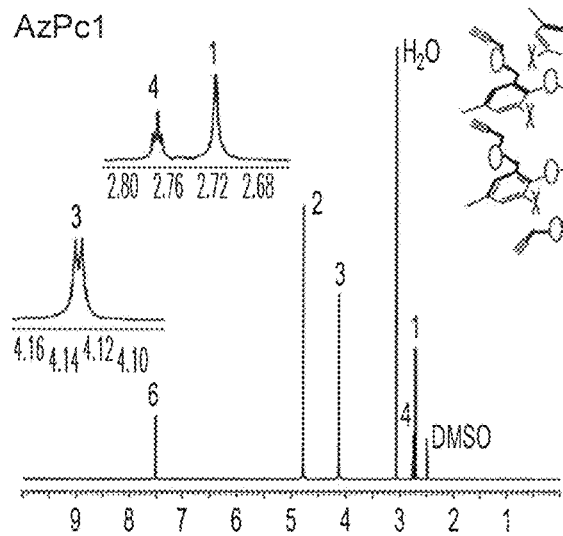
FIGS. 7A, 7C, 7E, 7G, and 7I show the $^1$H-spectra of AzaPc1, Pc2, Pc3, Pc4, and Pc-5, respectively.
Figure 7B:
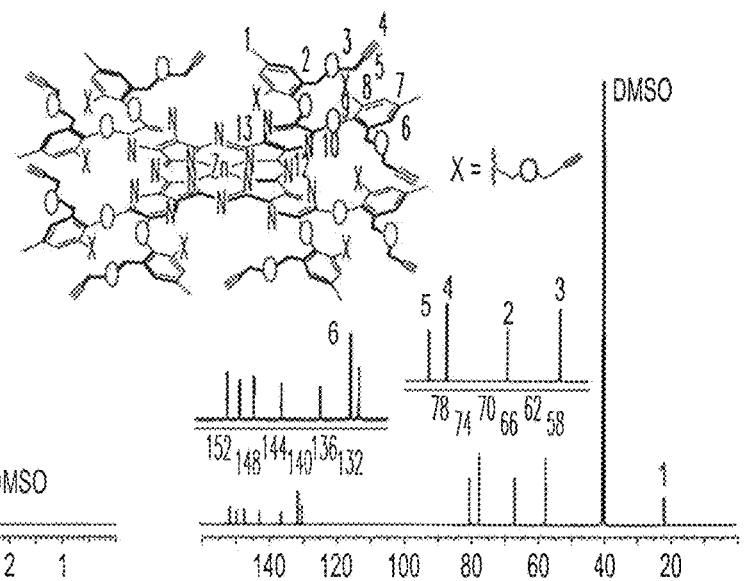
FIGS. 7B, 7D, 7F, 7H, and 7J show $^{13}$C-NMR spectra of AzaPc1, Pc2, Pc3, Pc4, and Pc-5, respectively.
Figure 7C:
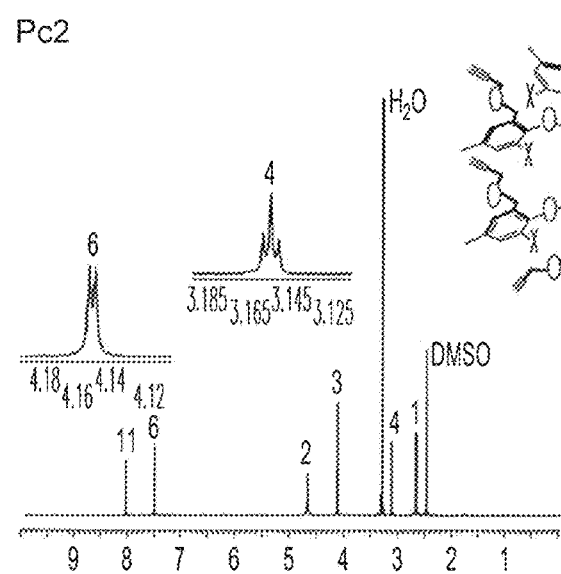
Figure 7D:
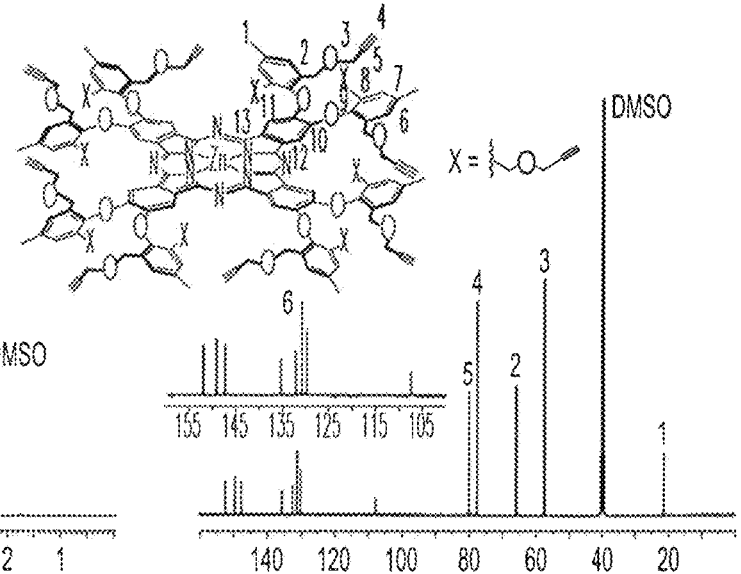

The structural features of AzaPc1 and Pc2-Pc5 synthesized according to the exemplary procedures above were characterized by NMR, MALDI-MS, FT-IR, UV-Vis, Fluorescence, DSC spectral data and CHNX elemental analysis. For example, in the $^1$H-NMR spectra (600 MHz, DMSO-d$_6$) of AzaPc1 (75° C.) and Pc2 (25° C.) (FIGS. 7A and 7C, respectively), terminal ethynyl protons (—C° C.H, H4) appear at 2.77 ppm (t, J=2.1 Hz) for AzaPc1 and at 3.15 ppm (t, J=2.7) for Pc2, while methyleneoxy protons (—CH$_2$OC H$_2$CCH, H3) appear at 4.13 ppm (d, J=2.7 Hz) and at 4.15 ppm (d, J=2.4 Hz) for AzaPc1 and Pc2, respectively. In $^{13}$C-NMR spectra (150 MHz, DMSO-d$_6$, 25° C.) (FIGS. 7B and 7D), terminal ethynyl carbons (—C°CH, C4) and (—C°CH, C5) appear in the region of ~77.0 ppm and ~80.0 ppm, and propargyl methylene carbons (—CH$_2$OCH$_2$CCH, C3) appear at 52.9 ppm and 57.2 ppm for AzaPc1 and Pc2, respectively.

Figures 7E, 7F:
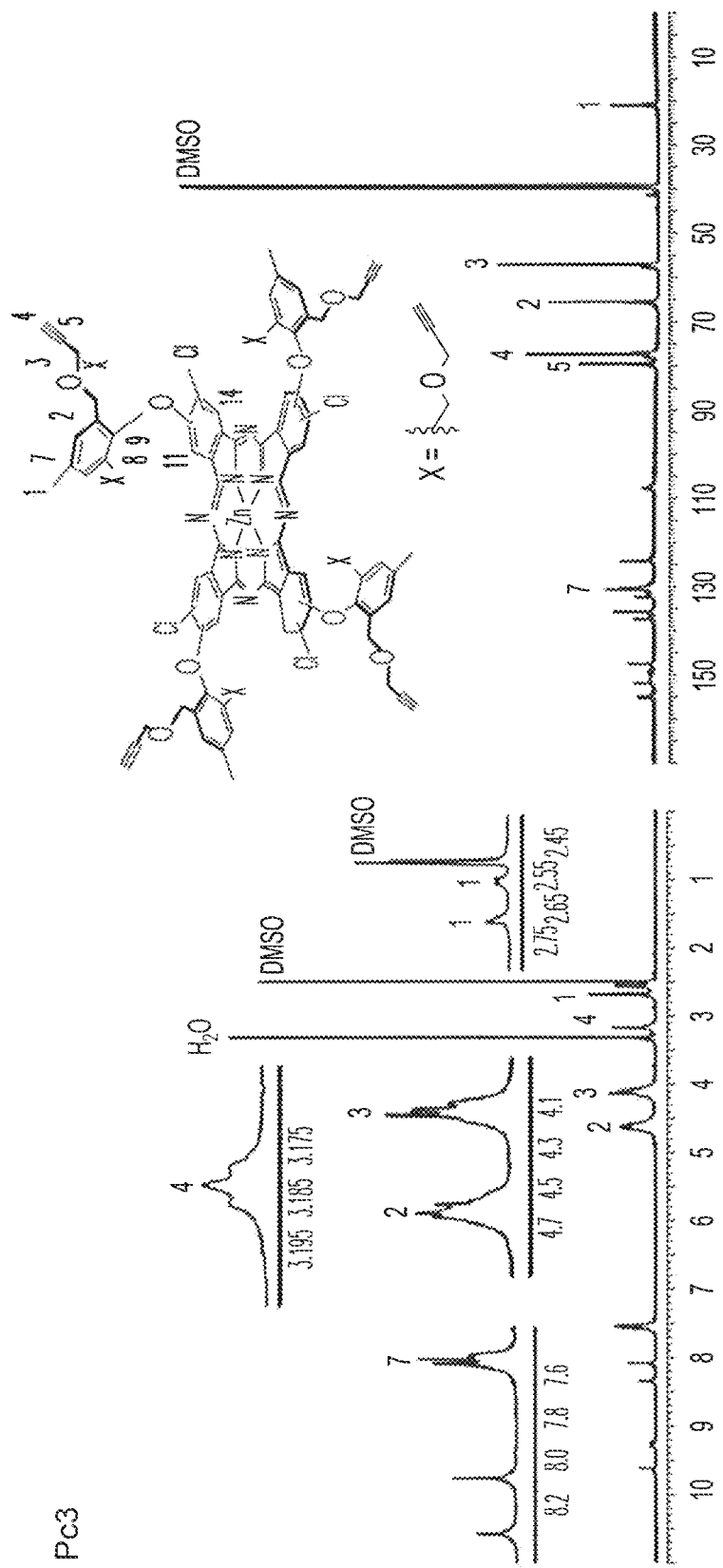

Correspondingly, in the $^1$H-NMR spectrum (600 MHz, DMSO-d$_6$, 25 0 C) of Pc3 (FIG. 7E), the benzylic protons (H1) appears as two sets of broad singlets (bs) at 2.57 ppm and 2.69 ppm, respectively, while the terminal alkyne protons (H4) (t, J=2.3 Hz) appear at 3.18 ppm. Methyleneoxy protons (H3 and H2) appear as broad multiplets in the region of 4.06-4.20 ppm and 4.52-4.72 ppm, respectively. The $^{13}$C-NMR spectrum (150 MHz, DMSO-d$_6$, 25° C.) (FIG. 7F), shows resonance at 77.3 ppm and 79.6 ppm corresponding to alkyne carbons (C4) and (C5), respectively, while resonance at 57.3 ppm and 65.6 ppm corresponds to propargyl methyleneoxy carbons (C3) and (C2), respectively.

Figure 7G:
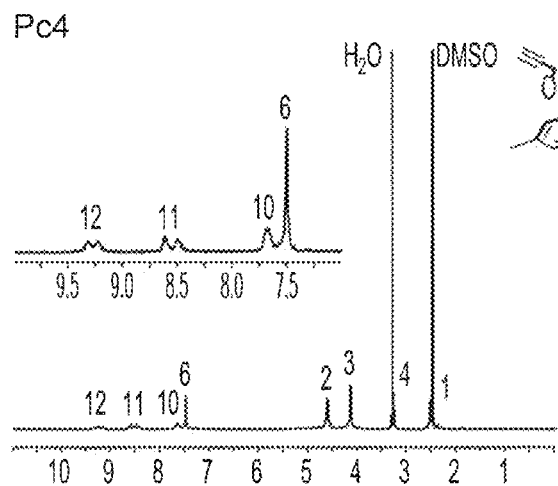
Figure 7H:
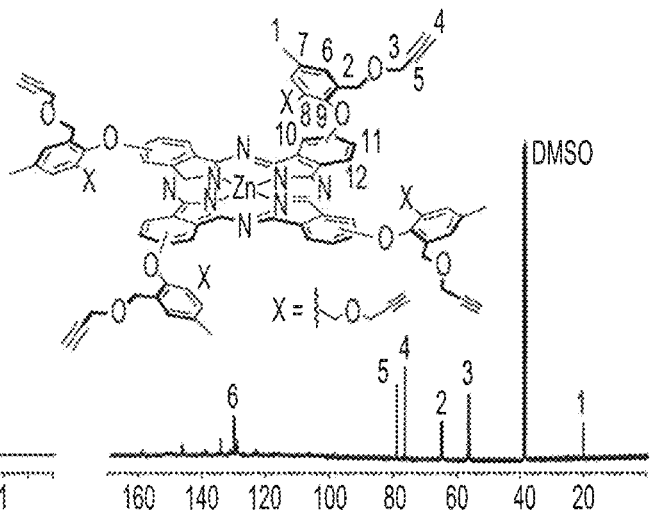
Figure 7I:
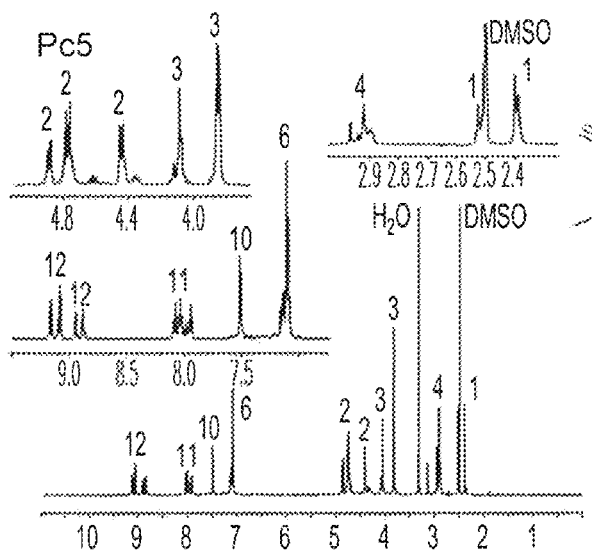
Figure 7J:
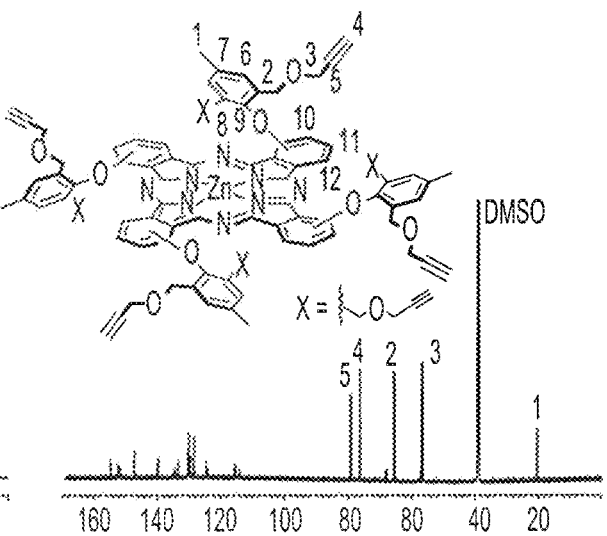

$^1$H-NMR spectra (600 MHz, DMSO-ds, 25 0° C.) of Pc4 and Pc5 (FIGS. 7G and 7I, respectively) evince benzylic protons (H1) as two sets of broad singlets (bs) at 2.52 ppm and 2.56 ppm for Pc4, and as multiple singlets at 2.39, 2.40 and 2.51 ppm for Pc5. The terminal ethynyl protons (H4) appear as a multiplet at 3.28 ppm for Pc4 and around ~2.89-2.91 ppm for Pc5. The methyleneoxy protons (H3 and H2) appear as broad singlets (bs) at 4.17 and 4.64 ppm, respectively, for Pc4, respectively, and as broad multiplets in the region of ~3.84-4.45 ppm for Pc5. The $^{13}$C-NMR spectra (150 MHz, DMSO-d$_6$, 25 0° C.) (FIGS. 7H and 7J) show alkyne carbons (C4) and (C5) at 77.3 and 79.9 ppm, respectively, for Pc4, and are found as more than one peak at 76.8, 76.9 and 77.0 ppm for C4 and at 79.8 and 80.0 ppm for C5 in Pc5. The varying breadth of proton signals in the $^1$H-NMR spectra for the asymmetric Pcs, i.e. Pc3-Pc5, is likely due to formation of different positional isomers during the cyclization reaction, which are hard to be separated or purified from each other via normal chromatography methods.

MS (MALDI-TOF:HCCA) of AzaPc1/Pc2-5 confirmed the chemical compositions by m/z (MALDI-TOF:HCCA) values of: observed 2523.4557 (M)+, calculated 2523.8188 (M)+ for AzaPc1; observed 2513.783 (M)+, calculated 2513.836 (M)+ for Pc2; observed 1684.3085 (M+H)+ calculated 1683.9100 (M+H)+ for Pc3; observed 1545.3420 (M)+, calculated 1545.4595 (M)+ for Pc4 and observed 1546.4673 (M+H)+, calculated 1546.3420 (M+H)+ for Pc5.

Example 7

Crystal Structures of AzaPc1 and Pc2-Pc5

Although growing stable single crystals of bulky molecular species can be very difficult, good quality crystals of ZnAzaPc1 and ZnPc2 were generated by suitable solvent diffusion methods and X-ray diffraction analysis and their crystal structures are depicted in FIGS. 8A-8B and 9A-9B, respectively.

The asymmetric unit of Pc2 crystal contains only a half section of the Pc structure due to internal symmetry exhibited by the molecule, and the complete structure was obtained by symmetry expansion. FIGS. 8A-8B and 9A-9B depict AzaPc1 and Pc2 structures, respectively, in solid state in two viewing positions, i.e., top and side views. Both AzaPc1 and Pc2 structures have a domed geometry with a zinc (II) ion occupying the top of the Pc/AzaPc planes. However, due to positional disorder, the zinc (II) ion in the Pc2 crystal is found to occupy both sides of the Pc plane with half occupancies each. In the case of AzaPc1, one methanol molecule is coordinated from the apex position to the zinc (II) ion, whereas, in the case of Pc2, such axial ligation of solvent molecule is not observed. However, two terminal ethynyl groups are occupied very close to the zinc (II) ion of the Pc2 so that appreciable Zn→C≡C—H coordination is possible in the crystal. Due to positional disorder, this Zn→C≡C—H coordination is observed from both sides of the Pc unit and hence appear to be propagated in a columnar manner.

Figure 10A:
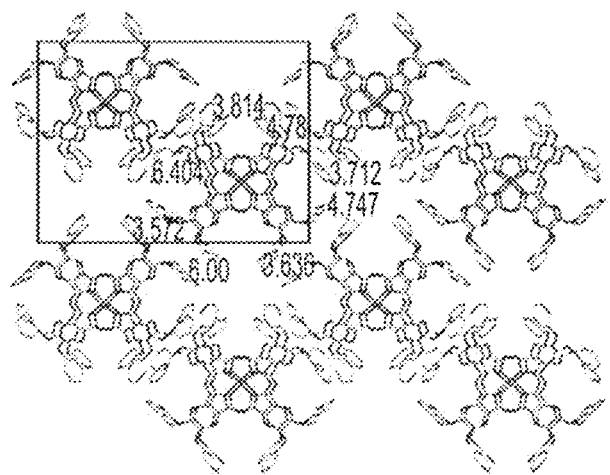
FIGS. 10A-10B show the network of AzaPc1 (10A) and Pc2 molecules (10B) in their crystal network showing the intermolecular π-π interactions through the phenoxyl moieties (the terminal substituents and hydrogens are hidden for clarity).
Figure 10B:
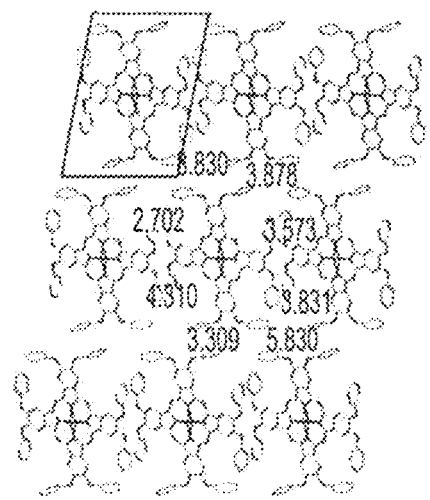

As in the case of precursors 3 and 4, the phenoxy substituents containing the propargyl units are oriented orthogonally with respect to both AzaPc1 (FIG. 8A) and Pc2 (FIG. 9A) systems. The terminal alkynes, which are substituted at the ortho positions of the phenoxyl moieties, are mostly oriented upward and downward from the macrocyclic systems in a random arrangement, as can be seen in the side views of the crystal structures depicted in FIGS. 8B and 9B. Such an orthogonal orientation of the phenoxy units and the resulting positions of the terminal alkyne moieties (up/down) with respect to the planar rims, as revealed from the crystal structure, clearly dismiss any possible face-to-face aggregation among the molecular assemblies. In both crystal structures, the Zn—Zn distance is more than 10 Å, which is too far to cause the undesired J-type core-to-core self-association. At the same time, the crystals exhibit a high degree of 2-dimensional intermolecular π-π interactions between adjacent phenoxyl moieties of the macrocycles, as demonstrated in FIGS. 10A-10B. All phenoxyl moieties in these crystals are oriented in face to face manner with another phenoxy unit of neighboring AzaPcs/Pcs. The distance between such phenoxy-phenoxy face to face orientations is within 4 Å in most fragments, which is sufficiently close for intermolecular π-π interactions. Such 2-dimensional π-π interactions between adjacent phenoxyl moieties provide sufficient stability to form crystal samples.

Example 8

Ground State Electronic Absorption Spectra of AzaPc1/Pc2-Pc5

Figure 11:
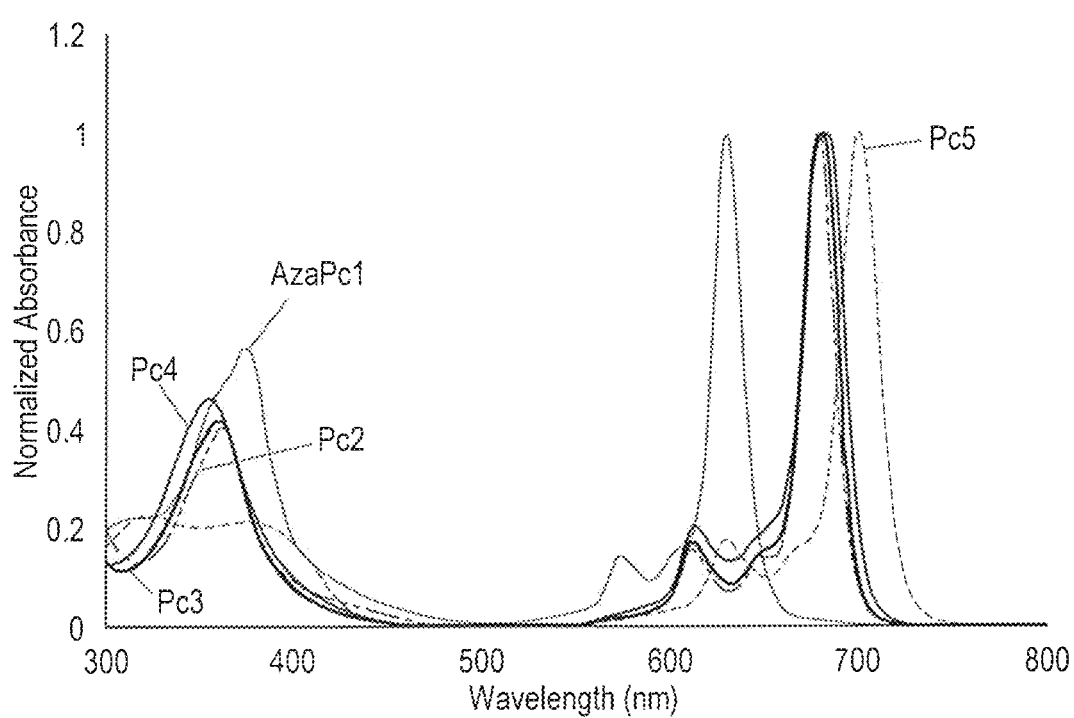
FIG. 11 shows the electronic absorption spectra of AzaPc1/Pc2-Pc5 in DMF.
Figure 12A:
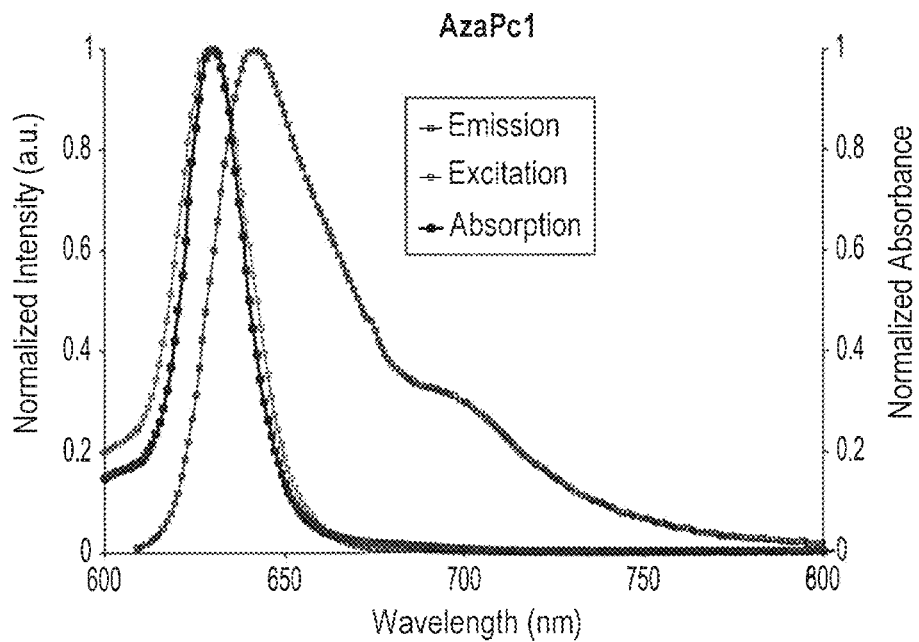
FIGS. 12A-12E show the absorption, excitation and emission spectra of AzaPc1/Pc2-Pc5 in DMF (excitation wavelength=600 nm for AzaPc1, 650 nm for Pc2-Pc4 and 668 nm for Pc5).
Figure 12B:
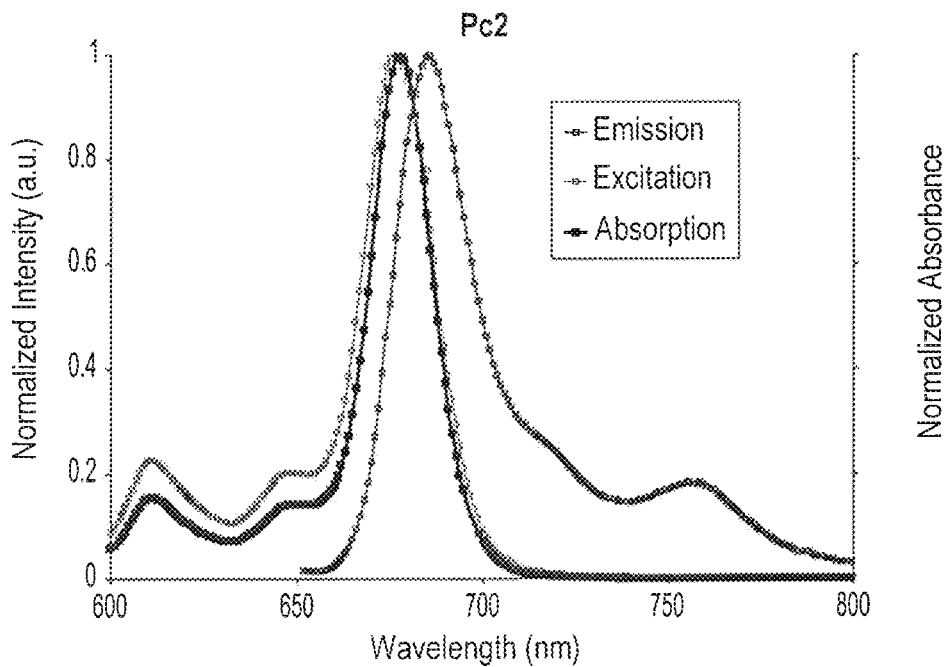
Figure 12C:
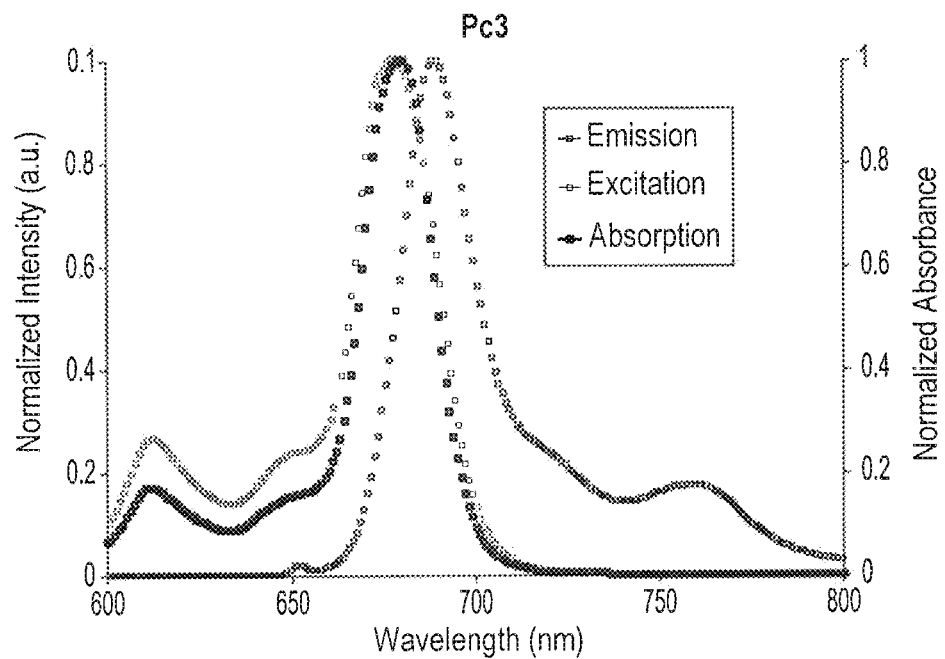
Figure 12D:
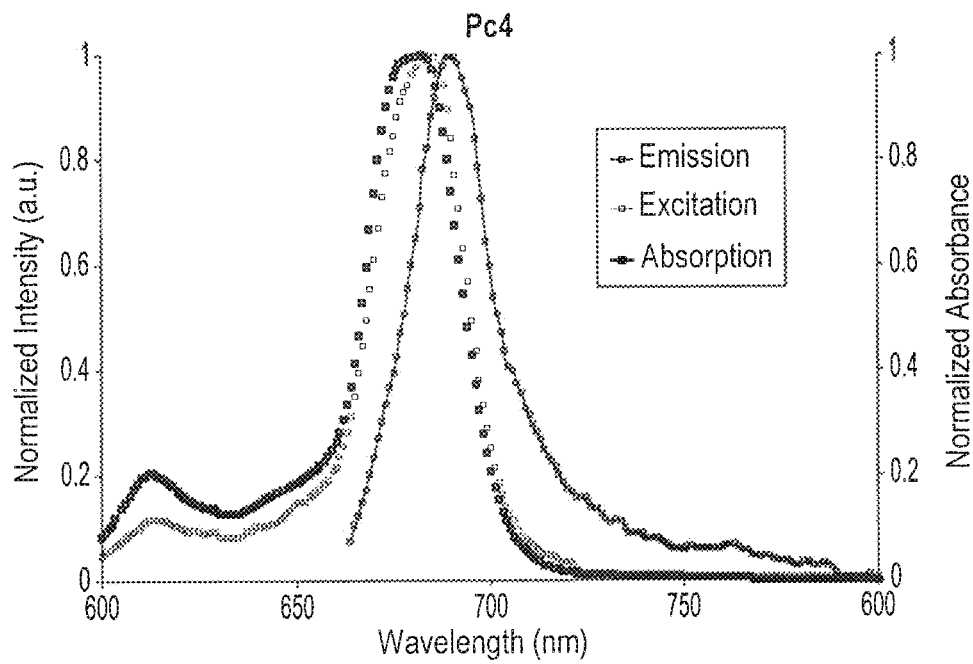
Figure 12E:
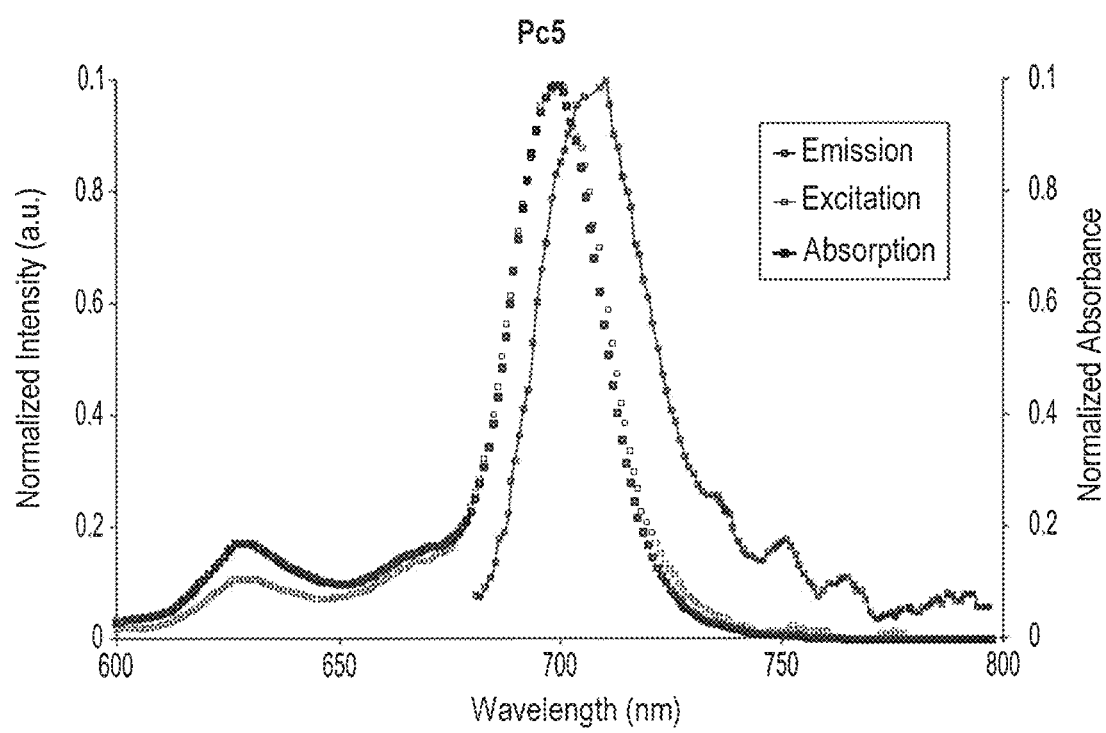

Electronic absorption, which is measured by UV-Vis spectroscopy, is one of the best spectroscopic techniques for determination of Pc formation and characterization of Pc compounds. Generally, two absorption bands are observed for Pc structures in their electronic absorption spectra. One band, known as Q, is observed at around 600-750 nm due to the π→π* transitions from the highest occupied molecular orbital (HOMO) to the lowest unoccupied molecular orbital (LUMO) of the Pc ring, while the other band, known as B, or the Soret band, is observed at around 300-450 nm due to transitions from deeper it levels to the LUMO. The ground state electronic absorption spectra of the studied novel Pcs were measured in DMF solution. The UV-vis spectra of these molecular structures are provided in FIG. 11, and peak results are summarized in Table 1.

The ground state electronic absorption spectra show monomeric behavior evidenced by single (narrow) Q band absorptions, which is typical for metallated complexes. The Q bands appear around 680 nm for the symmetric Pc2 and both asymmetric Pc3 and Pc4 in DMF (Table 1). On the other hand, the non-peripheral Pc5 show approximately 20 nm red-shifted Q band absorption at 700 nm when compared to the peripheral counterparts in the solvent (Table 1). The observed red spectral shifts are typical for Pc molecules with substituents at the non-peripheral positions and are presumably due to linear combinations of the atomic orbitals (LCAO) coefficients at the non-peripheral positions of the HOMO being greater than those at the peripheral positions. As a result, the HOMO level is destabilized more at the non-peripheral site than it is at the peripheral one. Essentially, the energy gap (ΔE) between the HOMO and LUMO becomes smaller, resulting in a bathochromic shift. The 49 nm blue shift for AzaPc1 is caused by the additional nitrogen atoms instead of CH groups in the Pc macrocyclic system. The B-bands are broad due to the superimposition of the B1 and B2 bands in the 340 to 380 nm region.

TABLE 1

Absorption, excitation and emission spectral data for AzaPc1/Pc2-Pc5 in DMF.

| Compd. | $\lambda_{max}$ (nm) | (log ε) | $\lambda_{Ex}$ (nm) | $\lambda_{Em}$ (nm) | Stokes shift $\Delta_{Stokes}$, (nm) |
|---|---|---|---|---|---|
| AzaPc1 | 629 | 5.07 | 629 | 639 | 10 |
| Pc2 | 678 | 5.33 | 679 | 683 | 4 |
| Pc3 | 679 | 5.33 | 678 | 686 | 8 |
| Pc4 | 680 | 5.21 | 682 | 688 | 6 |
| Pc5 | 700 | 5.10 | 700 | 707 | 7 |
| Std-ZnPc | 670 | 5.37 | 670 | 676 | 6 |

Example 9

Aggregation Studies

Macrocycle Pcs generate high aggregation tendencies due to the intermolecular interactions that take place between their 18 π-electrons. Accordingly, this self-association process would minimize their solubility in most solvent systems and therefore affect their spectroscopic, photophysical, photochemical, and electrochemical properties. Generally, aggregation is highly dependent on the concentration, temperature, nature of the substituents and/or their position and orientation with respect to the Pc skeleton, nature of the solvent media, and the central metal ion in the Pc-cores.

Pc molecules can form two types of aggregates in dissolved systems—H-type and J-type-depending on the nature, position and/or orientation of the substituents. In general, Pcs form H-type aggregates in solution, whereas J-type aggregates occur rarely. The formation of J-type aggregates among Pc structures is significant, since J-type aggregation is photoactive, while H-type aggregation is not.

The aggregation properties for the AzaPc1/Pc2-Pc5 compounds were determined in different organic solvents, namely, DCM, chloroform, DMF, DMSO, ethanol, methanol, THF and toluene. Interestingly, no aggregation for these assemblies was observed for any organic solvent used. However, small H-type aggregates were detected for Pc4 in methanol.

Aggregation behaviors for the AzaPc1/Pc2-Pc5 compounds were also investigated in DMF at different concentrations in order to establish a suitable concentration for further photophysical/photochemical studies. The Beer-Lambert law was obeyed at concentrations ranging from $1.0 \times 10^{-5}$ to $1.0 \times 10^{-6}$ M; no aggregation was seen for any of the compounds within this concentration range.

Fluorescence behaviors of the AzaPc1/Pc2-Pc5 compounds were evaluated in DMF solutions. FIGS. 12A-12E show absorption, fluorescence emission and excitation spectra of these complexes. The resulting studies in DMF showed similar fluorescence behavior in DMF in which the excitation spectra were similar to the absorption spectra and both were mirror images of the fluorescence emission spectra for all studied complexes. The proximity of the wavelength of each component of the Q-band absorption to the Q band maxima of the excitation spectra for all zinc (II) complexes suggested that the nuclear configurations of the ground and excited states are similar and not affected by excitation.

Excitation maxima appear at 629 nm for AzaPc1, 679 nm for Pc2, 678 nm for Pc3, 682 nm for Pc4 and 700 nm for Pc5 in DMF. Emission maxima appear at 639 nm, 683 nm, 686 nm, 688 nm and 707 nm for AzaPc1/Pc2-Pc5, respectively. The observed Stokes' shifts, which are differences between the excitation and emission wavelength maxima, are between 4 and 10 nm for all of the zinc (II) complexes (Table 1). The observed Stokes' shifts are consistent with those of typical zinc (II) phthalocyanine complexes.

Example 10

Fluorescence Quantum Yields and Lifetimes

Fluorescence emission occurs when an orbital electron of a photosensitizer relaxes from its singlet state to ground state upon emitting a photon of light. Fluorescence quantum yield ($\Phi_F$) indicates a measure of the efficiency of the fluorescence process and is defined as the ratio of the number of photons emitted to the number of photons absorbed. The fluorescence quantum yields ($\Phi_F$) may be determined using established methods described in existing literature. The $\Phi_F$ values of the present AzaPc1/Pc2-Pc5 compounds are typical for those phthalocyanine compounds (Table 2). Particularly, $\Phi_F$ values were measured to be 0.11 for AzaPc1, 0.16 for Pc2, 0.17 for Pc3, 0.14 for Pc4 and 0.11 for Pc5 in the exemplary DMF solvent system.

TABLE 2

Photophysical and photochemical parameters of the studied AzaPc1/Pc2-Pc5, as well as unsubstituted zinc(II) phthalocyanine DMSO.

| Compd. | $\Phi_F$ | $\tau_F$ (ns) | $\Phi_d$ (×10$^{-4}$) | $\Phi_\Delta$ |
|---|---|---|---|---|
| AzaPc1 | 0.14 | 2.46 | 4.30 | 0.63 |
| Pc2 | 0.16 | 3.30 | 1.58 | 0.60 |
| Pc3 | 0.17 | 2.84 | 1.40 | 0.60 |
| Pc4 | 0.14 | 3.37 | 1.12 | 0.57 |
| Pc5 | 0.11 | 2.61 | 2.77 | 0.88 |
| Std-ZnPc | 0.17 | 1.03 | 0.23 | 0.56 |

Fluorescence lifetime ($\tau_F$) refers to the average time that a molecule stays in its excited state before returning to its ground state by photon emission. The fluorescence lifetime values of the AzaPc1/Pc2-Pc5 compounds were determined by using time correlated single photon counting (TCSPC). All time-resolved fluorescence studies were carried out for the exemplary compounds in solution in DMF, and the fluorescence decays of the macrocycles were concluded in mono exponential curves. The fluorescence lifetime values were found to be 2.46 ns for AzaPc1, 3.30 ns for Pc2, 2.84 ns for Pc3, 3.37 ns for Pc4 and 2.61 ns for Pc5.

Example 11

Singlet Oxygen Quantum Yields

Transferring of energy from a triplet state of a photosensitizer such as Pc to ground state molecular oxygen leads to the production of singlet oxygen. There is a necessity of high efficiency of energy transfer between the excited triplet state of photosensitizer and the ground state of oxygen in order to generate large amounts of singlet oxygen, essential for PDT applications. The singlet oxygen quantum yield ($\Phi_A$) values give the amount of the generated singlet oxygen. This value is an indication of the potential provided by the compounds as photosensitizers in applications where singlet oxygen is required. The $\Phi_\Delta$ values for AzaPc1/Pc2-Pc5 were determined in DMF by a chemical method using 1,3-diphenylisobenzofuran (DPBF) as a quencher. The disappearance of DPBF at 414 nm was monitored using UV-Vis spectrophotometer. Many factors can be responsible for the magnitude of the determined singlet oxygen quantum yield, including triplet excited state energy, ability of substituents and solvents to quench the singlet oxygen, the triplet excited state lifetime and the efficiency of the energy transfer between the triplet excited state and the ground state of oxygen. Any changing was not observed in the Q band intensities of all cyclic complexes suggesting that all AzaPc1/Pc2-Pc5 did not show any decomposition during singlet oxygen studies.

All of the exemplary macrocyclic derivatives showed similar singlet oxygen generation, with $\Phi_A$ around 0.6, except for the non-peripheral substituted Pc5, which generated more singlet oxygen with $\Phi_A$ at 0.88, as well as longer wavelength absorption. All the tested cyclic structures, especially the non-peripheral substituted Pc5 derivative, appear to be suitable candidates as photosensitizers for cancer treatment by photodynamic therapy method due to their high singlet oxygen production abilities.

Example 12

Photodegradation Quantum Yields

Photodegradation is an indicator of the stability of compounds, which is useful for determining the photosensitizing ability of the compounds as PDT agents. The stability of photosensitizers under light irradiation is important for photochemical processes such as PDT because photosensitizers need to survive for a specific period in the body. Photodegradation degree can be detected by photodegradation quantum yield ($\Phi_d$), which depends on structure, light intensity, solvent used and concentration of a compound of interest. Photodegradation of a compound under light irradiation can be used to study the compound stability, which is important for those molecules intended for the application in photocatalytic reactions. Collapse of absorption spectra without any distortion of the shape of the absorption spectra confirms photo-degradation not associated with photo-transformation into different forms of Pcs absorbing light in the visible region. The spectral changes for all of the exemplary AzaPc1/Pc2-Pc5 compounds were determined in response to light irradiation, and photodegradation occurred without phototransformation, because only Q and B bands were decreased, i.e., no new band formation was observed.

Pc derivatives and their macrocyclic analogs generate singlet oxygen when they are illuminated by an appropriate light. The formed singlet oxygen is partially degraded by the Pc/Pc-analogs via photooxidation reactions. Generally, photodegradation of Pc/Pc-analog compounds by light irradiation results in formation of the phthalamide residue. The photodegradation behavior of AzaPc1/Pc2-Pc5 in DMF were determined. The $\Phi_d$ values of these novel systems are on the order of $10^{-4}$ (Table 2), consistent with values for other Pcs containing different metals and substituents.

Example 13

CuAAC Reaction with the AzaPc1/Pc2-Pc5 Compounds

The successfully synthesized novel zinc (II) macrocyclic complexes AzaPc1/Pc2-Pc5, may be applied as efficient molecular scaffolds toward the CuAAC reaction, as exemplified in the following experimental results. AzaPc1 was chosen to evaluate the CuAAC reaction with benzyl azide. The CuAAC reaction was carried out in the presence of DIPEA and a catalytic amount of Cu(I) in refluxed chloroform (see, reaction scheme below). Remarkably, the CuAAC reaction was effectively accomplished within 12 hrs resulting in the construction of sixteen 1,4-disubstituted 1,2,3-triazole linkages (AzaPc2) in excellent yield (92%). The structure of AzaPc2 was confirmed according to its respective NMR, MALDI-MS and FT-IR spectral data.

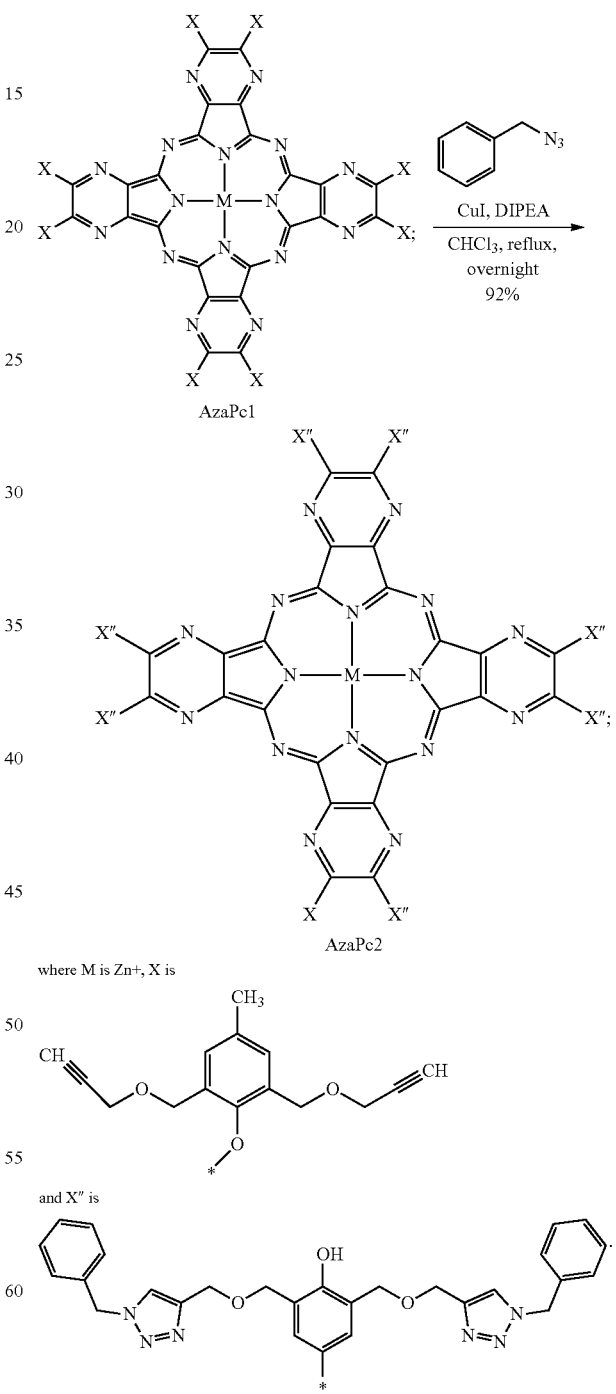

Figures 13A, 13B:
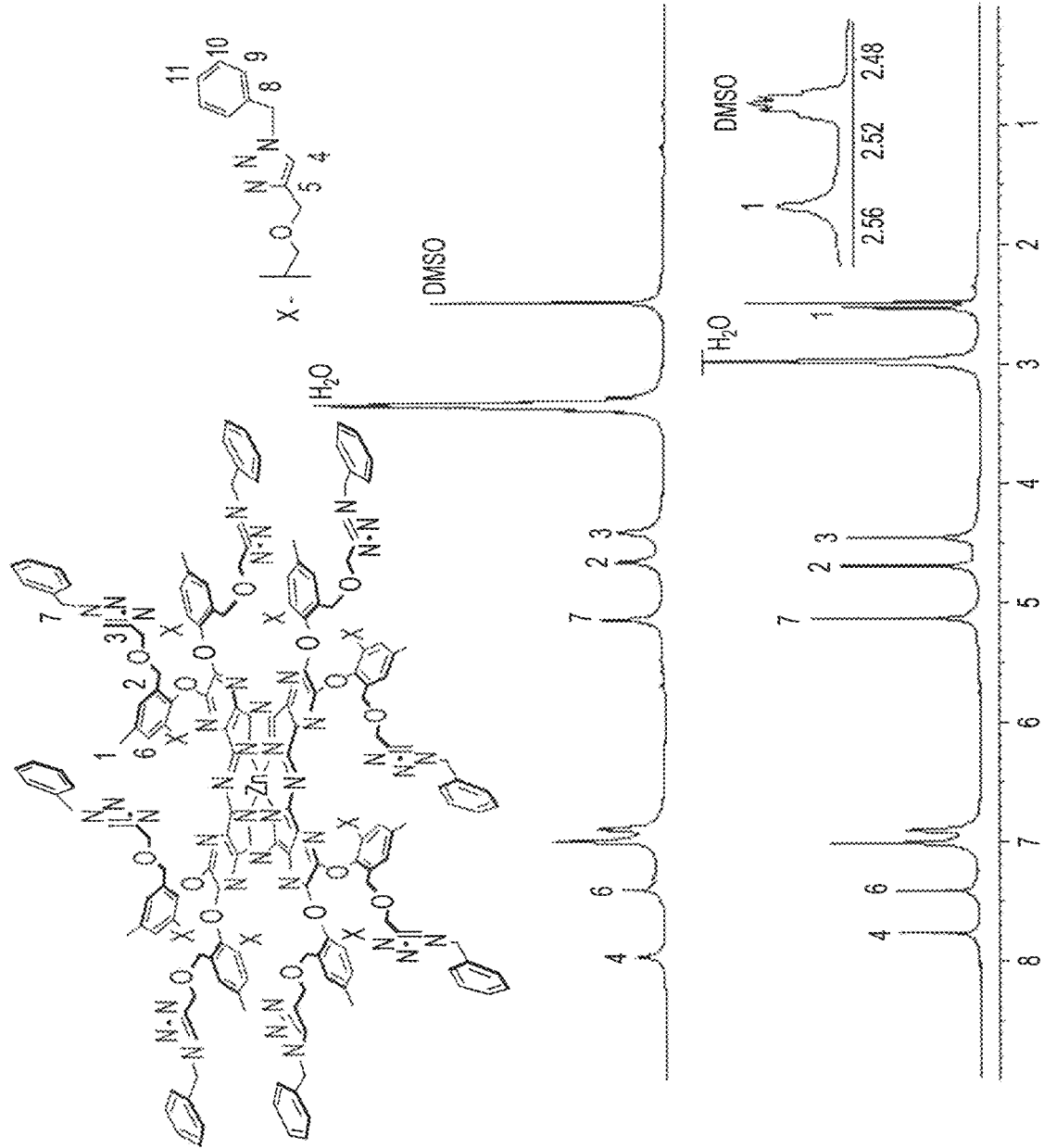
FIGS. 13A-13C show the full NMR spectra of AzaPc2.
Figure 13C:
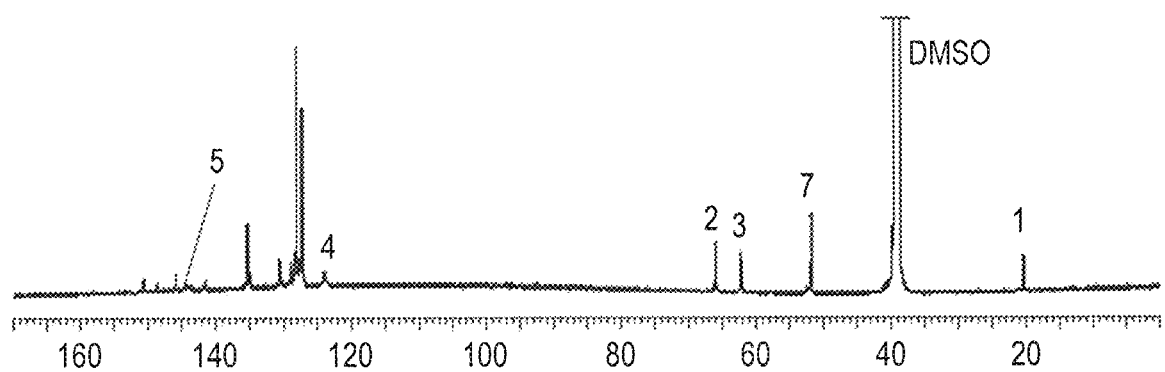

The $^1$H-NMR of AzaPc2 was evaluated at two different temperatures, i.e., 25° C. (FIG. 13A) and 95° C. (FIG. 13B), while the $^{13}$C-NMR was determined at 25° C. (FIG. 13C). From the $^1$H-NMR spectrum (600 MHz, DMSO-d$_6$, 95° C.) of AzaPc2, the disappearance of the terminal alkyne protons (—C≡C$\underline{H}$, H$_4$) from 3.18 ppm and the presence of two new resonance signals corresponded to the triazole protons (1H, H$_4$) at 7.79 ppm and the benzylic protons (—C$\underline{H}_2$C$_6$H$_5$, H$_7$) at 5.15 ppm, were used to confirm the structure. The benzylic protons (—C$\underline{H}_3$, H$_1$) were overlapped with the DMSO-d$_6$ solvent peak at 25° C. (FIG. 13A), while they were observed at 2.55 ppm at elevated temperature (FIG. 13B). In its $^{13}$C-NMR spectrum (150 MHz, DMSO-d$_6$, 25° C.), the disappearance of the ethynyl carbons (—C≡$\underline{C}$H, C$_4$, 77.3 ppm) and (—$\underline{C}$≡CH, C$_5$, 79.6 ppm) was observed, while the new triazole carbons C$_4$ and C$_5$ were found at 123.9 ppm and 144.3 ppm, respectively. The resonance at 52.3 ppm, 62.7 ppm and 66.7 ppm corresponded to the new benzylic (—$\underline{C}$H$_2$—C$_6$H$_5$, C$_7$), the methylenoxy (—CH$_2$O$\underline{C}$H$_2$CCH, C$_3$) and the methylene (—$\underline{C}$H$_2$OCH$_2$CCH, C$_2$) carbons, respectively.

The broadness of the proton signals at 25° C. can be explained by steric hindrance and slow motion of expected sandwich-like structure of AzaPc2 in solution. Multiple intramolecular π-π interactions may occur between adjacent phenyl groups based on the macrocyclic structure of AzaPc2 and the flexibility of chains joining the phenyl substituents could be dramatically minimized, causing the overall structure to move more slowly in solution. Elevating the temperature to 95° C. improved the sharpness and the intensities of all proton signals.

The heat added to raise the temperature to 95° C. presumably allows for breaking of possible intramolecular hydrophobic-hydrophobic interactions between the benzene rings. As a result, the phenyl-triazole chains become more flexible, making the AzaPc2 structure move more freely in solution. In addition to its well resolved $^1$H-NMR signals, UV-Vis analysis confirmed non-aggregated behavior of the AzaPc2 in solution.

Example 14

Synthesis of 2,6-Bis(Methylbromide)-p-Cresol (1):1

33% HBr in glacial acetic acid (60 mL) was added to 2,6-bis(hydroxylmethyl)-p-cresol (10 g, 6.0 mmol) and the mixture was stirred at room temperature for 24 hrs. After completion, the reaction mixture was diluted in 100 mL cold water allowing the product to precipitate out upon stirring for 30 min at room temperature. The resulting crude solid was filtered out using Buchner funnel which then re-crystallized out using (1:2) DCM/hexane solvent system as an eluent to afford 2,6-bis(methylbromide)-p-cresol (1) as a white crystals in 9.0 g (51% yield); mp is 123.6° C. Elemental analysis calculated (%) for C$_9$H$_{10}$Br$_2$O: C, 36.77; H, 3.43. Found: C, 36.70; H, 3.56; N; FT-IR, vmax/cm-1 3519.45, 3473.17, 3437.49, 1485.88, 1211.08; 1H-NMR (600 MHz, CDCl$_3$, 25 0 C): δ=2.27 (s, 3H), 4.55 (s, 4H), 5.44 (s, 1H), 7.09 (s, 2H); $^{13}$C-NMR (150 MHz, CDCl$_3$, 25 0 C): δ=20.5, 29.8, 125.2, 130.9, 132.0, 151.2; HRMS [M]+ calcd for C$_9$H$_{10}$Br$_2$O: 291.9098. found: 291.9093.

Example 15

Synthesis of 2,6-Bis(Methylpropargyl)-p-Cresol (2)

NaH (60%) (4.1 g, 102 mmol) was added slowly to a 100 mL ice cold dry THF. Propargyl alcohol (7.8 mL, 136 mmol) was then added dropwise to the solution and the reaction mixture was stirred for 30 min at 0° C. A solution of compound 1 (10 g, 34.0 mmol) in 50 mL dry THF was then added and the reaction was allowed to stir at room temperature for 12 hrs. After completion, the reaction mixture was quenched using MeOH followed by concentrating the solvent mixture under reduced pressure. The crude mixture was washed with 100 mL of water and extracted using EtOAc (2×50 mL) and the combined organic phase was collected and dried over anhydrous Na$_2$SO$_4$. The resulting crude product was subjected to column chromatography using (1:9) EtOAc/hexane solvent system as an eluent to obtain 2,6-bis(methylpropargyl)-p-cresol (2) as a pale yellow oil in 4.6 g (55% yield); Elemental analysis calculated (%) for C$_{15}$H$_{16}$O$_3$: C, 73.75; H, 6.60. Found: C, 72.50; H, 7.03; FT-IR, vmax/cm-1 3414.35, 3289.96, 2914.88, 2858.95; $^1$H-NMR (600 MHz, DMSO-d$_6$, 25 0 C): δ=2.20 (s, 3H), 3.46 (t, J=2.6 Hz, 2H), 4.17 (d, J=2.3 Hz, 41H), 4.50 (s, 4H), 6.97 (s, 2H), 8.34 (s, 1H); 13C-NMR (150 MHz, DMSO-d6, 25 0 C): δ=20.1, 56.9, 66.5, 77.2, 80.4, 124.7, 127.7, 129.0, 150.1; HRMS [M+Na]+ calcd for C$_{15}$H$_{16}$O$_3$Na: 267.0997, found: 267.0985.

Example 16

Synthesis of AzaPc-Precursor 3

Compound 2 (3.0 g, 12.1 mmol) was dissolved in 40 mL anhydrous acetonitrile. Anhydrous K$_2$CO$_3$ (2.8 g, 20.0 mmol) was then added to the solution and the mixture was allowed to stir for 10 min at room temperature. A solution of 2,3-dichloro-5,6-dicyano-1,4-pyrazine (1.0 g, 5.1 mmol) in 10 mL anhydrous acetonitrile was then added dropwise over a 5 min period of time and the reaction mixture was stirred overnight at room temperature. After completion, the formed salt was filtered out using Buchner funnel and acetonitrile was removed under reduced pressure. The crude product was purified by column chromatography using (1:9) EtOAc/hexane solvent system as an eluent to obtain the desired product 3 as a white solid in 3.0 g (97% yield); mp is 168.9° C. Elemental analysis calculated (%) for C$_{36}$H$_{30}$N$_4$O$_6$: C, 70.35; H, 4.92; N, 9.12. Found: C, 69.61; H, 5.01; N, 8.99; FT-IR, vmax/cm$^{-1}$ 3281.29, 2919.70, 2877.27, 2239.91, 2128.06; $^1$H-NMR (600 MHz, DMSO-d$_6$, 25° C.): δ=2.39 (s, 6H), 0.3.42 (t, J=2.6 Hz, 4H), 4.05 (d, J=2.3 Hz, 8H), 4.49 (s, 8H), 7.32 (s, 4H); $^{13}$C-NMR (150 MHz, DMSO-d$_6$, 25° C.): δ=20.5, 56.8, 66.2, 77.2, 79.8, 113.5, 123.7, 129.8, 130.2, 136.5, 145.4, 151.1; HRMS [M+Na]+ calcd for C$_{36}$H$_{30}$N$_4$O$_6$Na: 637.2063. found: 637.2037.

Example 17

Synthesis of Pc-Precursor 4

Compound 2 (3.0 g, 12.2 mmol) was dissolved in 40 mL anhydrous DMF. Anhydrous CsF (3.1 g, 20.2 mmol) was then added to the solution and the mixture was allowed to stir for 10 min at room temperature. A solution of 4,5-dichlorophthalonitrile (1.0 g, 5.1 mmol) in 10 mL anhydrous DMF was then added and the reaction mixture was heated to 100° C. for 48 hours. After completion, the formed salt was filtered out using Buchner funnel and the crude mixture was diluted in 100 mL water and extracted with DCM (2×50 mL). DCM was then concentrated under reduced pressure and the crude material was purified by column chromatography using (2:8) EtOAc/hexane solvent system as an eluent to obtain the desired product 4 as a white solid in 2.0 g (64% yield); mp is 117.7° C. Elemental analysis calculated (%) for $C_{38}H_{32}N_2O_6$: C, 74.49; H, 5.26; N, 4.57. Found: C, 74.66; H, 6.01; N, 4.26; FT-IR, vmax/cm-1 3289.96, 3265.86, 2871.49, 2230.27; $^1$H-NMR (600 MHz, DMSO-$d_6$, 25 0 C): δ=2.39 (s, 6H), 0.3.45 (t, J=2.6 Hz, 4H), 4.08 (d, J=2.6 Hz, 8H), 4.44 (s, 8H), 6.99 (s, 2H), 7.35 (s, 4H); $^{13}$C-NMR (150 MHz, DMSO-$d_6$, 25 0 C): δ=20.5, 57.1, 65.6, 77.2, 79.7, 108.8, 115.6, 119.2, 130.2, 130.7, 136.0, 146.1, 150.4; HRMS [M+Na]+ calcd for $C_{38}H_{32}N_2O_6Na$: 635.2158. found: 635.2122.

Example 18

Synthesis of Pc-Precursor 5

Compound 2 (1.5 g, 6.1 mmol) was dissolved in 40 mL anhydrous DMF. Anhydrous CsF (1.9 g, 12.2 mmol) was then added to the solution and the mixture was allowed to stir for 10 min at room temperature. A solution of 4,5-dichlorophthalonitrile (1.0 g, 5.1 mmol) in 10 mL anhydrous DMF was then added and the reaction mixture was stirred for 24 hrs at room temperature. After completion, the salt was filtered out using Buchner funnel and the crude mixture was diluted in 100 mL water and extracted with DCM (2×50 mL). DCM was then concentrated under reduced pressure and the crude material was purified by column chromatography using (2:8) EtOAc/hexane solvent system as an eluent to obtain the desired product 5 as a white solid in 1.7 g (85% yield); mp is 106.2° C. Elemental analysis calculated (%) for $C_{23}H_{17}ClN_2O_3$: C, 68.23; H, 4.23; N, 6.92. Found: C, 68.03; H, 4.22; N, 6.78; FT-IR, vmax/cm$^{-1}$ 3297.68, 2883.06, 2611.14, 2232.20; 1H-NMR (600 MHz, DMSO-$d_6$, 25 0 C): δ=2.38 (s, 3H), 0.3.33 (t, J=2.3 Hz, 211), 4.02 (t, J=2.3 Hz, 4H), 4.32 (dd, J=10.9, 35.0 Hz, 4H), 7.09 (s, 1H), 7.35 (s, 2H), 8.47 (s, 1H); $^{13}$C-NMR (150 MHz, DMSO-$d_6$, 25 0 C): δ=20.5, 57.7, 77.2, 79.5, 108.5, 114.8, 114.9, 115.0, 119.9, 126.8, 130.0, 131.4, 135.6, 136.4, 146.6, 157.6; HRMS [M]+ calcd for $C_{23}H_{17}ClN_2O_3$: 404.0928. found: 404.0922.

Example 19

Synthesis of Pc-Precursor 6

Compound 2 (3.4 g, 13.9 mmol) was dissolved in 40 mL anhydrous DMF. Anhydrous $K_2CO_3$ (3.2 g, 23.1 mmol) was then added to the solution and the mixture was allowed to stir for 10 min at room temperature. A solution of 3-nitrophthalonitrile (1.0 g, 5.8 mmol) in 10 mL anhydrous DMF was then added and the reaction mixture was heated to 100° C. for 5 hrs. After completion, the salt was filtered out using Buchner funnel and the crude mixture was diluted in 100 mL water and extracted with DCM (2×50 mL). DCM was then concentrated under reduced pressure and the crude material was purified by column chromatography using (2:8) EtOAc/hexane solvent system as an eluent to obtain the desired product 6 as a white solid in 1.9 g (89% yield); mp is 318.4 0° C. Elemental analysis calculated (%) for $C_{23}H_{18}N_2O_3$: C, 74.58; H, 4.90; N, 7.56. Found: C, 74.40; H, 5.38; N, 7.37; FT-IR, vmax/cm$^{-1}$ 3270.68, 2231.24, 2114.56; $^1$H-NMR (600 MHz, DMSO-$d_6$, 25° C.): d=2.37 (s, 3H), 0.3.35 (t, J=2.3 Hz, 2H), 4.03 (d, J=2.6 Hz, 4H), 4.33 (s, 4H), 7.18 (dd, J=2.6, 8.7 Hz, 1H), 7.32 (s, 2H), 7.52 (d, J=2.6 Hz, $1H_1$), 8.01 (d, J=9.0 Hz, 1H); $^{13}$C-NMR (150 MHz, DMSO-$d_6$, 25 0 C): δ=20.5, 57.1, 65.6, 77.3, 79.7, 107.5, 115.5, 116.0, 116.4, 120.3, 120.8, 130.2, 130.9, 136.0, 146.1, 146.4, 161.6; HRMS [M]+ calcd for $C_{23}H_{18}N_2O_3$: 370.1317 found: 370.1312.

Example 20

Synthesis of Pc-Precursor 7

Compound 2 (3.4 g, 13.9 mmol) was dissolved in 40 mL anhydrous DMF. Anhydrous $K_2CO_3$ (3.2 g, 23.1 mmol) was then added to the solution and the mixture was allowed to stir for 10 min at room temperature. A solution of 3-nitrophthalonitrile (1.0 g, 5.8 mmol) in 10 mL anhydrous DMF was then added and the reaction mixture was heated to 100° C. for 5 hrs. After completion, the salt was filtered out using Buchner funnel and the crude mixture was diluted in 100 mL water and extracted with DCM (2×50 mL). DCM was then concentrated under reduced pressure and the crude material was purified by column chromatography using (2:8) EtOAc/hexane solvent as an eluent to obtain the desired product 7 as a white solid in 1.3 g (85% yield); mp is 314.3° C. Elemental analysis calculated (%) for $C_{23}H_{18}N_2O_3$: C, 74.58; H, 4.90; N, 7.56. Found: C, 74.08; 11, 4.95; N, 7.46; FT-IR, vmax/cm$^{-1}$ 3273.57, 2864.74, 2236.06, 2114.56; $^1$H-NMR (600 MHz, DMSO-$d_6$, 25 0 C): δ=2.37 (s, 3H), 3.34 (t, J=2.6 Hz, 2H), 4.04 (t, J=2.3 Hz, 41-), 4.36 (d, J=9.0 Hz, 4H), 6.85-6.87 (dd, J=0.8, 8.3 Hz, 1H), 7.34 (s, 2H), 7.69-7.75 (m, 2H); 13C-NMR (150 MHz, DMSO-$d_6$, 25 0 C): δ=20.4, 57.1, 65.6, 77.3, 79.5, 102.9, 113.3, 115.5, 115.7, 119.6, 127.3, 130.2, 131.0, 135.6, 136.3, 146.4, 160.5; HRMS [M+Na]+ calcd for $C_{23}H_{18}N_2O_3Na$: 370.1317; found: 370.1312.

Example 21

Synthesis of Multi-Valent Propargyl Azaphthalocyanine (AzaPc1)

A mixture of compound 3 (2.5 g, 4.1 mmol) and $Zn(OAc)_2$ (186.3 mg, 1.0 mmol) were dissolved in 3 mL pentanol. A catalytic amount of N,N-dimethylethanolamine was then added to the solution and the reaction mixture was heated to 140° C. for 1 hour. The reaction mixture was then precipitated from methanol and the solid material was filtered out using Buchner funnel. The crude product was subjected to column chromatography using (1:19) EtOAc/DCM solvent system as an eluent to afford the desired product AzaPc1 as a dark green solid in 710 mg (28% yield); mp is 282.0° C. Elemental analysis calculated (%) for $C_{144}H_{120}N_{16}O_{24}Zn$: C, 68.52; H, 4.79; N, 8.88. Found: C, 66.84; H, 4.73; N, 8.53; UV-Vis, nm (log e) (in DMF): 629 (5.07), 573 (4.18), 374 (4.78); FT-IR, vmax/cm$^{-1}$ 3439.42, 3286.11, 2919.70, 2858.95; $^1$H-NMR (600 MHz, DMSO-$d_6$, 75 0° C.): δ=2.72 (s, 24H), 2.77 (t, J=2.1 Hz, 16H), 4.13 (d, J=2.7 Hz, 32H), 4.78 (s, 32H), 7.52 (s, 16H); $^{13}$C-NMR (150 MHz, DMSO-$d_6$, 25 0 C): δ=21.1, 52.9, 66.2, 76.8, 80.0, 129.6, 130.8, 135.7, 142.1, 146.6, 148.9, 150.9; MS (MALDI-TOF:HCCA): m/z=Calc. for $C_{144}H_{123}N_{16}O_{24}Zn$: 2523.8188 [M]+, found: 2523.4557.

Example 22

Synthesis of Multi-Valent Propargyl Phthalocyanine (Pc2)

A mixture of compound 4 (2.5 g, 4.0 mmol) and $Zn(OAc)_2$ (187.4 mg, 1.0 mmol) were dissolved in 3 mL pentanol. A catalytic amount of N,N-dimethylethanolamine was then added to the solution and the reaction mixture was heated to 140° C. for 5 hours. The reaction mixture was then precipitated from methanol and the solid material was filtered out using Buchner funnel. The crude product was subjected to column chromatography using (1:19) EtOAc/DCM solvent system as an eluent to afford the desired product Pc2 as a dark green solid in 1.1 g (43% yield); mp is 284.3° C. Elemental analysis calculated (%) for $C_{152}H_{128}N_8O_{24}Zn$: C, 72.56; H, 5.13; N, 4.45. Found: C, 71.90; 11, 5.21; N, 4.17; UV-Vis, nm (log e) (in DMF): 678 (5.33), 611 (4.38), 361 (4.80); FT-IR, $v_{max}$/cm$^{-1}$ 3437.49, 3286.11, 2913.91, 2855.10; 1H-NMR (600 MHz, DMSO-d$_6$, 25 0 C): δ=2.69 (s, 24H), 3.15 (t, J=2.7 Hz, 16H), 4.15 (d, J=2.4 Hz, 321H), 4.69 (s, 32H), 7.53 (s, 16H), 8.06 (s, 8H); $^{13}$C-NMR (150 MHz, DMSO-d$_6$, 25 0 C): δ=21.1, 57.2, 65.6, 77.3, 79.7, 107.4, 129.7, 130.9, 132.2, 135.4, 147.4, 149.3, 152.1; MS (MALDI-TOF:HCCAP: m/z=Calc. for $C_{152}H_{128}N_8O_{24}Zn$: 2513.836 [M]+. found: 2513.783.

Example 23

Synthesis of Multi-Valent Propargyl Phthalocyanine (Pc3)

A mixture of compound 5 (2.5 g, 6.2 mmol) and Zn(OAc)$_2$ (283.8 mg, 1.5 mmol) were dissolved in 3 mL pentanol. A catalytic amount of N,N-dimethylethanolamine was then added to the solution and the reaction mixture was heated to 140° C. for 5 hours. The reaction mixture was then precipitated from methanol and the solid material was filtered out using Buchner funnel. The crude product was subjected to column chromatography using (1:19) EtOAc/DCM solvent system as an eluent to afford the desired product Pc3 as a dark green solid in 755 mg (29% yield); mp is 199.3° C. Elemental analysis calculated (%) for $C_{92}H_{68}C_4N_8O_{12}Zn$: C, 65.59; H, 4.07; N, 6.65. Found: C, 65.71; H, 4.94; N, 5.69; UV-Vis, nm (log e) (in DMF): 679 (5.33), 612 (4.57), 361 (4.95); FT-IR, vmax/cm$^{-1}$ 3290.93, 2853.17, 2116.49; 1H-NMR (600 MHz, DMSO-d$_6$, 25 0 C): δ=2.57 (s, 6H), 2.69 (bs, 6H), 3.18 (t, J=2.3, 811H), 4.06-4.20 (m, 16H), 4.52-4.72 (m, 16H), 7.49-7.59 (m, 8H), 8.09 (s, 211), 8.35 (s, 21H), 9.25 (bs, 1H), 9.29 (s, 11-), 9.62 (s, 1H); $^{13}$C-NMR (150 MHz, DMSO-d$_6$, 25 0 C): δ=21.0, 21.1, 57.3, 65.6, 65.7, 77.3, 79.6, 107.8, 107.9, 124.1, 124.5, 130.3, 130.7, 132.1, 132.2, 135.7, 137.4, 137.6, 152.1, 154.9, 155.3; MS (MALDI-TOF:HCCAP: m/z=Calc. for $C_{92}H_{69}C_{14}N_8O_{12}Zn$: 1684.3085 [M+H]+. found: 1683.9100.

Example 24

Synthesis of Multi-Valent Propargyl Phthalocyanine (Pc4)

A mixture of compound 7 (2.5 g, 6.8 mmol) and Zn(OAc)2 (310 mg, 1.7 mmol) were dissolved in 3 mL pentanol. A catalytic amount of N,N-dimethylethanolamine was then added to the solution and the reaction mixture was heated to 140° C. for 5 hours. The reaction mixture was then precipitated from methanol and the solid material was filtered out using a Buchner funnel. The crude product was subjected to column chromatography using (1:19) EtOAc/DCM solvent system as an eluent to afford the desired product Pc4 as a dark green solid in 740 mg (28% yield); mp is 374.4° C. Elemental analysis calculated (%) for $C_{92}H_{72}N_8O_{12}Zn$: C, 71.43; H, 4.69; N, 7.24. Found: C, 71.60; H, 5.59; N, 6.73; UV-Vis, nm (log e) (in DMF): 700 (5.10), 629 (4.33), 377 (4.43); FT-IR, vmax/cm$^{-1}$ 3285.14, 2854.13, 2114.56; 1H-NMR (600 MHz, DMSO-d$_6$, 25 0 C): δ=2.56 (bs, 1211), 3.28 (m, 8H), 4.17 (bs, 16H), 4.64 (bs, 16H), 7.50 (bs, 8H), 7.68 (bs, 4H), 8.50 (bs, 2H), 8.62 (bs, 211), 9.23 (bs, 2H), 9.32 (bs, 2H); $^{13}$C-NMR (150 MHz, DMSO-d$_6$, 25 0 C): δ=20.7, 20.8, 57.4, 65.4, 65.8, 77.3, 79.9, 107.4, 117.4, 124.2, 129.9, 130.9, 132.0, 135.7, 139.5, 147.3, 159.9; MS (MALDI-TOF:HCCAP: m/z=Calc. for $C_{92}H_{72}N_8O_{12}Zn$: 1545.4595 [M]+. found: 1545.3420.

Example 25

Synthesis of Multi-Valent Propargyl Phthalocyanine (Pc4)

A mixture of compound 6 (2.5 g, 6.8 mmol) and Zn(OAc)2 (310 mg, 1.7 mmol) were dissolved in 3 mL pentanol. A catalytic amount of N,N-dimethylethanolamine was then added to the solution and the reaction mixture was heated to 140° C. for 5 hours. The reaction mixture was then precipitated from methanol and the solid material was filtered out using Buchner funnel. The crude product was subjected to column chromatography using (1:19) EtOAc/DCM solvent system as an eluent to afford the desired product Pc5 as a dark green solid in 680 mg (26% yield); mp is >300° C. Elemental analysis calculated (%) for $C_{92}H_{72}N_8O_{12}Zn$: C, 71.43; H, 4.69; N, 7.24. Found: C, 71.60; H, 5.59; N, 6.73; UV-Vis, nm (log e) (in DMF): 680 (5.21), 613 (4.52), 355 (4.87); FT-IR, vmax/cm-1 3287.07, 2857.99, 2113.60; $^1$H-NMR (600 MHz, DMSO-d6, 25 0 C): δ=2.39 (bs, 1411), 2.40 (bs, 16H), 2.51 (bs, 10H), 2.53 (bs, 14H), 2.89-2.91 (m, 10H), 2.92 (m, 1211), 3.84 (m, 12H), 3.85-3.87 (m, 22H), 4.07-4.12 (m, 22H), 4.43-4.45 (m, 20H), 4.73-4.81 (m, 32H), 4.88-4.90 (m, 12H), 7.10-7.13 (m, 26H), 7.14-7.18 (m, 1211), 7.51-7.54 (m, 12H), 7.94-8.01 (m, 6H), 8.03-8.06 (m, 6H), 8.09 (t, J=7.5 Hz, 4H); $^{13}$C-NMR (150 MHz, DMSO-d$_6$, 25 0 C): δ=20.6, 20.7, 57.0, 57.1, 57.3, 65.9, 66.1, 76.8, 76.9, 77.0, 79.8, 80.0, 114.4, 114.5, 114.9, 115.0, 116.1, 116.5, 124.5, 124.6, 124.7, 125.1, 125.2, 128.7, 129.0, 130.6, 131.0, 131.1, 131.2, 134.0, 134.1, 135.1, 135.2, 140.4, 140.6, 140.7, 141.0, 147.9, 148.1, 152.3, 152.7, 153.3, 155.1, 155.2, 155.4; MS (MALDI-TOF:HCCAP: m/z=Calc. for $C_{92}H_{73}N_8O_{12}Zn$: 1546.4673 [M+H]+, found: 1546.3420.

Example 26

Synthesis of Multi-Valent Benzyl Phthalocyanine (AzaPc2) Via the CuAAC Reaction

In a proof of concept of the utility of the Pc/Pc-analog compounds of embodiments of the subject matter as substrates for reactions such as the CuAAC reaction, multi-valent benzyl phthalocyanine (AzaPc2) was synthesized from AzaPc1 via the CuAAC reaction.

AzaPc1 (0.1 mmol) and benzyl azide (32.0 equiv.) were dissolved in 40 mL chloroform. CuI (10 mol %) and DIPEA (6.0 equiv.) were then added to the solution and the reaction mixture was refluxed overnight. After completion, the reaction mixture was washed with ammonium hydroxide solution and the organic layer was collected and dried over anhydrous Na$_2$SO$_4$. Chloroform was removed over reduced pressure and the product was purified by column chromatography using (19:1) MeOH/DCM solvent system as an eluent to afford the desired product AzaPc2 as a green solid in 428 mg (92% yield); Elemental analysis calculated (%) for $C_{256}H_{232}N_{64}O_{24}Zn$: C, 66.06; H, 5.02; N, 19.26. Found: C, 66.20; H, 4.99; N, 19.01; FT-IR, vmax/cm$^{-1}$ 3449.06, 3133.76, 2920.66, 2859.92, 1398.14; $^1$H-NMR (600 MHz, DMSO-d6, 95° C.): δ=2.55 (s, 24H), 2.77, 4.48 (s, 32H), 4.72 (s, 32H), 5.15 (s, 32H), 6.91-6.94 (m, 64H), 7.01-7.03 (m, 96H), 7.43 (s, 16H), 7.79 (s, 32H); $^{13}$C-NMR (150 MHz, DMSO-$d_6$, 25 0 C): δ=20.7, 52.3, 62.7, 66.7, 123.9, 127.3, 127.6, 128.2, 128.5, 129.1, 130.8, 135.3, 141.8, 144.3, 146.1, 148.9, 150.8; MS (MALDI-TOF:HCCA): m/z=Calc. for $C_{256}H_{232}N_{64}NaO_{24}Zn$: 4674.8191 [M+Na]+. found: 4674.5570.

Example 27

Crystal Structures of Propargyl Substituted AzaPc-Precursor (3) and Pc-Precursors (4-7)

Pyrazine and phthalonitrile precursors having both mono- and di-substituted phenoxyl groups with terminal ethynyl units were analyzed by single crystal X-ray diffraction technique. This included a pyrazine system possessing two phenoxyl groups which contain terminal alkyne moieties at ortho positions (3) and the corresponding pthalonitrile (4) having the same substitution features. The crystal structures of those phthalonitrile units which consist of only mono-substituted phenoxyl groups have also been reported in this study. These phenoxyl groups are either at the peripheral position with respect to the pthalonitrile plane (5 & 6) or at the non-peripheral position (7). In compound 5, there is additional chlorine which is substituted at the second peripheral position. The crystal structure of all these precursors provides valuable information regarding the orientation of phenoxyl units and terminal ethynyl with respect to the phthalonitrile plane. The crystallographic parameters the structures of the pyrazine and phthalonitrile substrates with propargyl moieties, as obtained from single crystal diffraction analysis, are given in Tables 3 and 4.

The plane of the phenoxyl ring having the terminal alkynyl groups are oriented almost perpendicular to the plane of the phenyl rings containing the nitrile groups (the corresponding torsion angles are presented in Table 5). This is due to the restricted rotation imposed on phenoxyl moieties by the bulky alkyne substituents which are presented at the ortho positions of the phenyl groups. Such a blocked rotation caused by the propargyl chains is sufficient for ensuring the non-aggregating feature for those Pc systems which will be synthesized from these unique molecules by the metal mediated cyclization. The terminal propargyl groups having sufficient chain length for flexible orientations are projected randomly in their crystal network. Their packing is very efficient so that without having any solvent co-crystallization, these crystals are stable enough for diffraction studies.

TABLE 3

Summary of the nature and various crystallographic parameters of crystal samples of pyrazine precursor (compound 3) and phthalonitrile (compound 4).

| Crystal sample | 3 | 4 |
|---|---|---|
| Crystal data | | |
| Chemical formula | $C_{36}H_{30}N_4O_6$ | $C_{38}H_{32}N_2O_6$ |
| Mr | 614.64 | 612.65 |
| Crystal system, space group | Monoclinic, P2$_1$/n | Monoclinic, P2$_1$/n |
| Temperature (K) | 296 | 296 |
| a, b, c (Å) | 12.8709 (4), 15.6947 (4), 16.5272 (5) | 12.6219 (11), 16.3765 (13), 16.6547 (14) |
| β (°) | 92.507 (2) | 100.607 (4) |
| V (Å3) | 3335.38 (17) | 3383.7 (5) |
| Z | 4 | 4 |
| Radiation type | Cu Kα | Cu Kα |
| μ (mm−1) | 0.69 | 0.66 |
| Crystal size (mm) | 0.30 × 0.20 × 0.07 | 0.22 × 0.11 × 0.05 |
| Data collection | | |
| Diffractometer | Bruker X8 Prospector | Brisker X8 Prospector |
| Absorption correction | Multi-scan SADABS V2008/1 (Bruker) | Multi-scan SADABS V2008/1 (Bruker) |
| Tmin, Tmax | 0.70, 0.96 | 0.60, 0.87 |
| No. of measured, independent & observed [I > 2σ(I)] reflections | 28049, 5828, 2669 | 23446, 5674, 4020 |
| Rint | 0.154 | 0.058 |
| (sin θ/λ)max (Å$^{-1}$) | 0.595 | 0.593 |
| Refinement | | |
| R[F2 > 2σ(F2)], wR(F2), S | 0.071, 0.260, 1.00 | 0.083, 0.207, 1.13 |
| No. of reflections | 5828 | 5674 |
| No. of parameters | 417 | 427 |
| No. of restraints | 31 | 54 |
| H-atom treatment | Constrained | Constrained |
| Δρmax, Δρmin (e Å$^{-3}$) | 0.44, −0.26 | 0.24, −0.28 |

TABLE 4

Summary of the nature and various crystallographic parameters of crystal samples of mono substitutes phenoxyl phthalonitriles (compounds 5, 6 and 7).

| Crystal data | | | |
|---|---|---|---|
| Chemical formula | $C_{23}H_{17}ClN_2O_3$ | $C_{46}H_{36}N_4O_6$ | $C_{23}H_{18}N_2O_3$ |
| Mr | 404.84 | 740.79 | 370.41 |
| Crystal system, space Group | Monoclinic, P21/c | Triclinic, P-1 | Triclinic, P-1 |
| Temperature (K) | 296 | 150 | 293 |
| a, b, c (Å) | 14.9291 (5), 10.5173 (3), 14.4180 (4) | 8.4034 (9), 10.6002 (11), 12.8112 (14) | 10.4756 (7), 11.1851 (8), 11.4936 (8) |
| β (°) | 111.081 (1) | 65.879 (5), 83.922 (6), 82.056 (6) | 101.408 (7), 107.744 (8), 117.153 (9) |
| V (Å3) | 2112.31 (11) | 1030.01 (19) | 1047.2 (2) |
| Z | 4 | 1 | 2 |
| Radiation type | Cu Kα | Mo Kα | Mo Kα |
| μ (mm−1) | 1.81 | 0.08 | 0.08 |
| Crystal size (mm) | 0.39 × 0.29 × 0.13 | 0.20 × 0.16 × 0.05 | 0.21 × 0.20 × 0.15 |
| Data collection | | | |
| Diffractometer | Bruker X8 Prospector | Rigaku R-AXIS RAPID | Rigaku R-AXIS RAPID |
| Absorption correction | Multi-scan SADABS V2008/1 (Bruker) | Multi-scan ABSCOR (Rigaku, 1995) | Multi-scan ABSCOR (Rigaku, 1995) |
| Tmin, Tmax | 0.56, 0.79 | 0.984, 0.996 | 0.683, 0.988 |
| No. of measured, independent and observed [I > 2σ(I)] reflections | 19063, 3554, 3117 | 8066, 3608, 2152 | 9418, 4249, 2930 |
| Rint | 0.041 | 0.039 | 0.02 |
| (sin θ/λ)max (Å$^{-1}$) | 0.595 | 0.595 | 0.624 |
| Refinement | | | |
| R[F2 > 2σ(F2)], wR(F2), S | 0.048, 0.160, 0.86 | 0.106, 0.348, 1.24 | 0.046, 0.176, 1.14 |
| No. of reflections | 3554 | 3608 | 4249 |
| No. of parameters | 263 | 291 | 254 |
| H-atom treatment | Independent constrained | Constrained | Constrained |
| Δρmax, Δρmin (e Å$^{-3}$) | 0.48, −0.52 | 0.85, −0.73 | 0.30, −0.19 |

TABLE 5

List of torsion angles corresponds to the phenoxy with respect to the di-nitrile plane in 3 to 7

| Atom list | Torston angle | Atom list | Torsion angle |
|---|---|---|---|
| Crystal: 3 | | | |
| C8—C7—O1—C5 | 87.89 | C12—C7—O1—C5 | −96.37 |
| C23—C22—O4—C6 | 96.37 | C27—C22—O4—C6 | −92.47 |
| Crystal: 4 | | | |
| C10—C9—O1—C7 | 96.63 | C14—C9—O1—C7 | −90.70 |
| C25—C24—O4—C6 | 98.79 | C29—C24—O4—C6 | −87.50 |
| Crystal: 5 | | | |
| C10—C9—O2—C6 | 87.99 | C14—C9—O2—C6 | −97.05 |
| Crystal: 6 | | | |
| C8—C7—O1—C1 | 91.05 | C12—C7—O1—C1 | −95.42 |
| Crystal: 7 | | | |
| C10—C9—O1—C1 | 91.89 | C14—C9—O1—C1 | −91.04 |

The crystallographic parameters of the crystal structures of AzaPc1 and Pc2 containing hexadeca-propargyl functionalities are provided in Table 6. The asymmetric unit of Pc2 crystal contains only half of the phthalocyanine due to internal symmetry of the molecule and the complete structure could be obtained by symmetry expansion. In both AzaPc1 and Pc2, the Zinc (II) ion occupied at the top of the Pc plane and the azaphthalocyanine/phthalocyanine macrocycles is observed to have a domed geometry. The Pc2 molecule in crystal network exhibited positional disorder at the center and due to this disorder, the Zn (11) ion in Pc2 crystal is found to occupy both sides of the Pc plane, with almost half occupancies each. In the case of AzaPc1, one methanol molecule is coordinated from the apex position to the Zinc ion, where as in Pc2 such axial ligation of solvent molecule is not observed. However, two terminal alkynyl groups are occupied very close to the Zinc (II) ion of the Pc2 so that appreciable Zn→C≡C—H coordination could be possible in its crystal. Due to positional disorder, this Zn→C≡C—H coordination is observed from both sides of the Pc unit and hence is seen to propagate along the crystal in columnar manner.

TABLE 6

Summary of the nature and various crystallographic parameters of crystal samples AzaPc1 and Pc2.

| Crystal sample | AzaPc1 | Pc2 |
|---|---|---|
| Crystal data | | |
| Chemical formula | $C_{152}H_{128}N_8O_{24}Zn$ | $C_{147}H_{132}N_{16}O_{27}Zn$ |
| $M_r$ | 2515.99 | 2620.06 |
| Crystal system, space group | Triclinic, P-1 | Monoclinic, P2$_1$/a |
| Temperature (K) | 150 | 150 |
| a, b, c (Å) | 12.8844 (13), 13.9073 (13), 20.6328 (19) | 23.940 (11), 28.050 (13), 23.991 (11) |
| α, β, γ (°) | 98.862 (7), 106.525 (7), 94.899 (7) | 119.850 (8) |
| V (Å$^3$) | 3469.4 (6) | 13973 (11) |
| Z | 1 | 4 |
| Radiation type | Mo Kα | Mo Kα |
| μ (mm$^{-1}$) | 0.25 | 0.25 |
| Crystal size (mm) | 0.21 × 0.12 × 0.09 | 0.22 × 0.19 × 0.03 |
| Data collection | | |
| Diffractometer | Rigaku R-AXIS RAPID | Rigaku R-AXIS RAPID |
| Absorption correction | Multi-scan ABSCOR (Rigaku, 1995) | Multi-scan ABSCOR (Rigaku, 1995) |
| $T_{min}$, $T_{max}$ | 0.950, 0.978 | 0.947, 0.993 |
| No. of measured, independent and observed [I > 2σ(I)] reflections | 27487, 12186, 6351 | 102734, 24158, 14696 |
| $R_{int}$ | 0.032 | 0.081 |
| (sin θ/λ)max (Å$^{-1}$) | 0.595 | 0.596 |
| Refinement | | |
| R[F$^2$ > 2σ(F$^2$)], wR(F$^2$), S | 0.138, 0.420, 1.45 | 0.129, 0.365, 1.26 |
| No. of parameters | 842 | 1798 |
| No. of restraints | 241 | 431 |
| H-atom treatment | Constrained | Independent and constrained |
| Δρmax, Δρmin (e Å$^{-3}$) | 1.17, −0.76 | 2.86, −0.77 |

The crystal network of AzaPc1 contains methanol molecules as the space-filling solvents which are co-crystallized along with the AzaPc molecules during crystal growth. The peak densities of these solvent molecules were very weak and not properly refined anisotropically during structural refinement. So these solvent molecules in AzaPc1 are only refined isotropically. In the case of Pc2, some electron density is present within the void places by the presence of co-crystallized solvent molecules. Due to poor crystal quality these peaks could not be assigned to the corresponding solvent atoms properly. Therefore these unassigned solvent peaks were removed from the final refinement using the SQUEEZE technique by PLATON.

As in the case of their pyrazine and phthalonitrile precursors, the phenoxy units containing the propargyl units are oriented orthogonal with respect to the plane of Pc ring. These terminal alkynes which are presented at the ortho positions of the phenoxyl moieties are mostly oriented upward and downward from the macrocycle planes in a random arrangement. The orthogonal orientation of the phenoxy units and the resulting positions of the terminal propargyl moieties (up/down) with respect to the macrocycle planes as revealed from the crystal structures clearly dismiss any possible face to face Pc aggregation among these Pc molecules. In both these crystals, the Zn—Zn distance is more than 10 Å which is too far to cause the undesired J-type core to core Pc self-aggregation. However, unlike their precursor molecules, the special disposition of propargyl groups in AzaPc1 and Pc2 crystals are not exactly similar as the terminal alkynes are more widely oriented in Pc2 than AzaPc1. This difference could be presumably due to the difference in axial coordination, variations in crystallization conditions, etc.

The packing of both AzaPc1 and Pc2 molecules in their crystal form is very and efficient by utilizing intermolecular π-π interactions with adjacent Pcs. All phenoxyl moieties in these crystals are oriented in face- to face manner with other phenoxy units of neighboring Pcs. It is observed that the distance between such phenoxy-phenoxy face to face orientation is within 4 Å in most fragments which is well sufficient for intermolecular π-π interactions. Such 2-dimensional π-π interactions between adjacent phenoxyl moieties provide sufficient stability to these crystal samples.

In the case of AzaPc, the arrangements of AzaPc1 molecules are in such a way that along a- and c-directions all molecules in each row are arranged in the same manner and direction, whereas along b-direction the are arranged in zig-zag manner with adjacent AzaPcs being inverted to each other. At the same time, in the case of Pc2 crystals, Pc molecules in each row along all 3 directions namely a-, b-, c-, are oriented in the same way. In synthesizing the present compounds, varying the reaction conditions, i.e., solvent polarity, concentration, temperature, pressure, base, can play an important role in enhancing the cyclization process and improving the overall yield of the desired products (Table 7).

TABLE 7

Reaction conditions applied for the synthesis of Pc building blocks.

| Entry | Metal | Reagent | Solvent (mL) | Temp. (° C.) | Time |
|---|---|---|---|---|---|
| 1 | $H_2$ | $NH_3$ | DMAE | Reflux | 7 h |
| 2 | | DBU | MeOH | Reflux | 18 h |
| 3 | | DBU | EtOH | Reflux | 18 h |
| 4 | | DBU | n-Hexan-1-ol | 100 | 18 h |
| 5 | | DBU | C6H13O(CH2)2OH | 100 | 18 h |
| 6 | | DBN | bulk | 200 | 4 h |
| 7 | | THP | bulk | 200 | 4 h |
| 8 | | DBN | n-Pentan-1-ol | Reflux | 36 h |
| 9 | | DMAE | n-Pentan-1-ol | Reflux | 36 h |
| 10 | | Sodium benzenetellurolate | EtOH | Reflux | 12 h |
| 11 | | Li | DMAE | 50 | 24 h |
| 12 | | Li | DMAE | 20 | 24 h |
| 13 | | Hydroquinone | MeOH | 90 | 70 h |
| 14 | | Hydroquinone | bulk | 275 | |
| 15 | | LiCl electrosynthesis | EtOH | 75 | |
| 16 | | Electrochemical 40 mA, 42 V | DMAE | 189 | 1 h |
| 17 | | LiCl Photo-electrosynthesis | EtOH | 75 | |
| 18 | $Li_2Pc$ | Li | n-pentan-1-ol | Reflux | 30 min |
| 19 | BePc | Etched Be metal | | 230 | |
| 20 | $Na_2Pc$ | Na | n-pentan-1-ol | Reflux | 10 min |
| 21 | MgPc | Mg turnings | | Reflux | 6 h |
| 22 | | Etched Mg turnings | | 230 | 2 h |
| 23 | | $MgCl_2$, DBU | pentanol | Reflux | 6 h |
| 24 | | Mg turnings | $NH_3$ | 250 | 2 h |
| 25 | AlOHPc | 1. $Al(OBu)_3$, urea | Butan-1-ol | 140 | 6 h |
| | | 2. $H_2SO_4$ | | 100 | 2 h |
| 26 | AlClPc | $AlCl_3$ | Quinoline | Reflux | 0.5 or 1 h |
| 27 | $SiCl_2Pc$ | $SiCl_4$ | Quinoline | | |
| 28 | $K_2Pc$ | K metal | Iso-pentan-1-ol | Reflux | 1 h |
| 29 | CaPc | Ca metal | Iso-pentan-1-ol | Reflux | 5 h |
| 30 | ScClPc | $ScCl_3$ | 1-chloronaphthalene | Reflux | 5 h |
| 31 | ScPc2 | $Sc(OAc)_3$ | | 300 | 2 h |
| 32 | TiOPc | 1. $TiCl_3$ | 1-chloronaphthalene | 250 | |
| | | 2. Pyridine/$NH_4OH$ | | Reflux | |
| 33 | | 1. $Ti(OBu)_4$/urea | Octan-1-ol | 150 | 6 h |
| | | 2. MeOH | | Reflux | 30 min |

In addition to the efficient 2-dimensional π-π interactions between adjacent phenoxyl moieties among the AzaPc1 and Pc2 molecules, the crystals are also stabilized by van der waals interactions between adjacent atoms. The possible short contact interactions (within the van der waals range) were observed in these crystals.

In conclusion, the crystal structures of hexadeca-propargyl functionalized zinc(II) phthalocyanine (Pc2) and their corresponding azaphthalocyanine analogue (AzaPc1) have been obtained from single crystal X-ray diffraction technique along with the structures of some pyrazine and phthalonitrile precursor units having terminal propargyl moieties (3-7). Based on the crystal structure it could be confirmed that for all these precursors, the plane of the phenoxy ring having terminal alkyne groups are oriented perpendicular to the plane of the phenyl moiety containing the nitrile groups. This is due to the restricted rotation imposed on phenoxyl moieties by the bulky alkynyl substituents which are presented at the ortho positions of the phenyl groups. This orthogonal orientation is observed in all precursor species irrespective of the number of phenoxy substitution. In both AzaPc1 and Pc2, the macrocycle system is observed to have a domed geometry with Zinc (II) ion occupied at the top of the Pc plane. Similar to the case of their precursors, the phenoxy units containing the propargyl units are oriented orthogonal with respect to the plane of Pc ring in both AzaPc1 and Pc2 and the terminal alkyne moieties are oriented upward and downward from the Pc rim in a random arrangement. Such an orthogonal orientation of the phenoxy units and the resulting positions of the terminal propargyl moieties (up/down) with respect to the Pc plane dismiss undesired face to face Pc aggregation among these Pc/AzaPc molecules. At the same time, these crystals are characterized by high degree of 2-dimensional π-π interactions between adjacent phenoxyl moieties of AzaPc/Pc macrocycles which provide sufficient stability to these crystal samples.

It is to be understood that the propargyl-functionalized macrocyclic compounds are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A propargyl-functionalized macrocyclic compound having the formula:
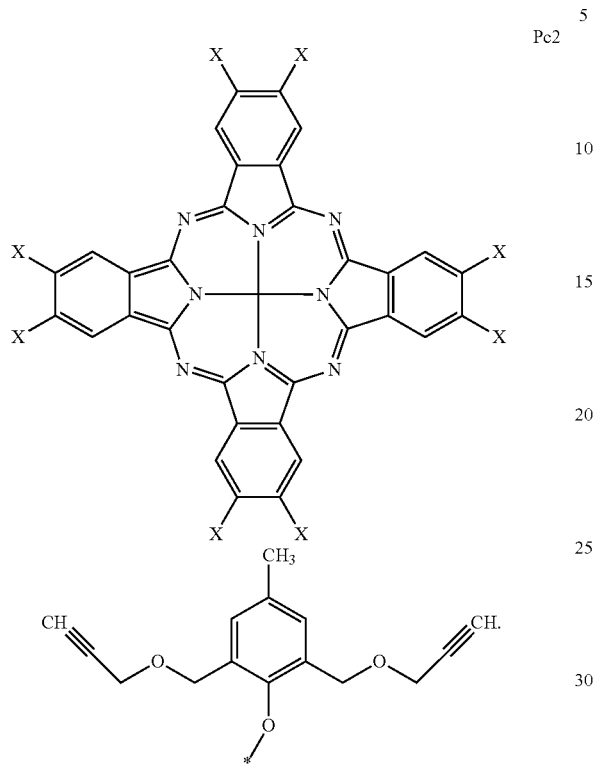
Pc2
2. The compound according to claim 1, wherein M is Zn2+.